US010576140B2

(12) United States Patent
Tinker

(10) Patent No.: US 10,576,140 B2
(45) Date of Patent: Mar. 3, 2020

(54) CHOLERA TOXIN CHIMERA AND ITS USE AS A STAPH VACCINE

(71) Applicant: **

(56) References Cited

OTHER PUBLICATIONS

Harakuni et al., "Heteropentameric Cholera Toxin B Subunit Chimeric Molecules Genetically Fused to a Vaccine Antigen Induce Systemic and Mucosal Immune Responses: a Potential New Strategy to Target Recombinant Vaccine Antigens to Mucosal Immune Systems", Infection and Immunity, vol. 73, No. 9, pp. 5654-5665, Sep. 2005.

Schaffer et al., "Immunization with *Staphylococcus aureus* Clumping Factor B, a Major Determinant in Nasal Carriage, Reduces Nasal Colonization in a Murine Model", Infection and Immunity, vol. 74, No. 4, pp. 2145-2153, Apr. 2006.

Narita et al. "Role of Interleukin-17A in Cell-Mediated Protection against *Staphylococcus aureus* Infection in Mice Immunized with the Fibrinogen-Binding Domain of Clumping Factor A" Infection and Immunity, vol. 78, No. 10, pp. 4234-4242, Oct. 2010.

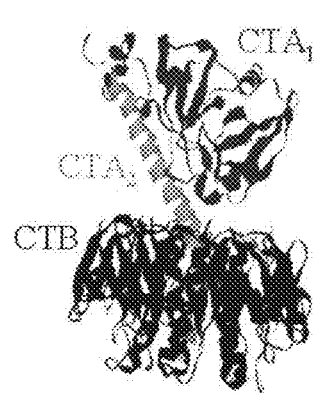 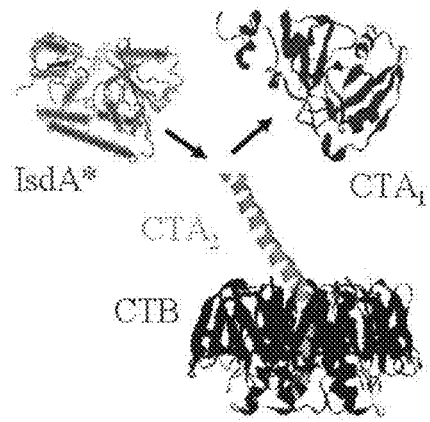 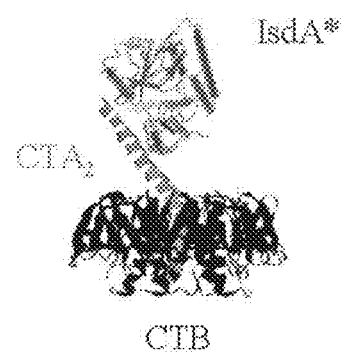
*FIG. 1A*   *FIG. 1B*   *FIG. 1C*
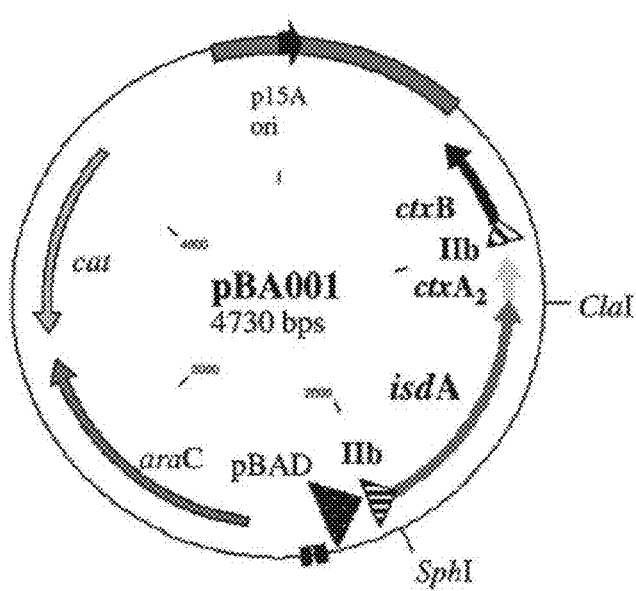
*FIG. 2*

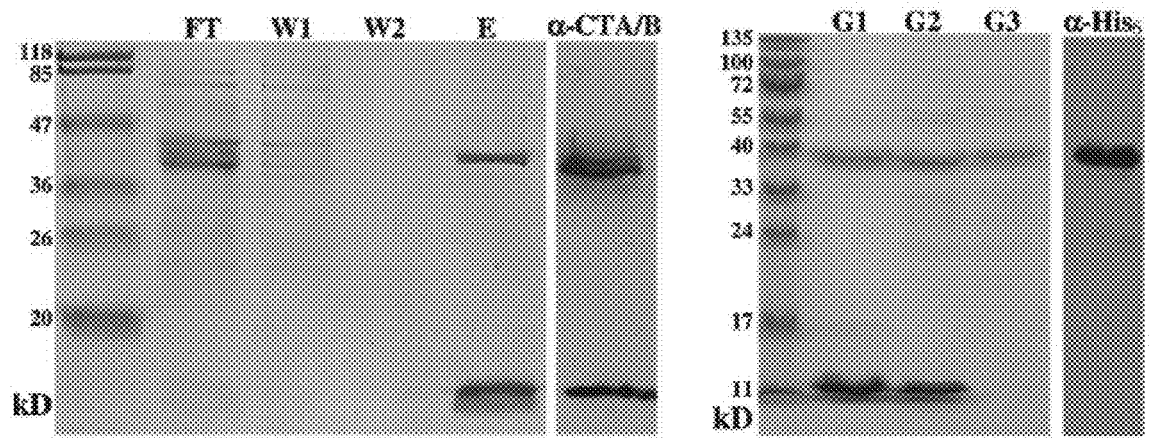
*FIG. 3A*  *FIG. 3B*
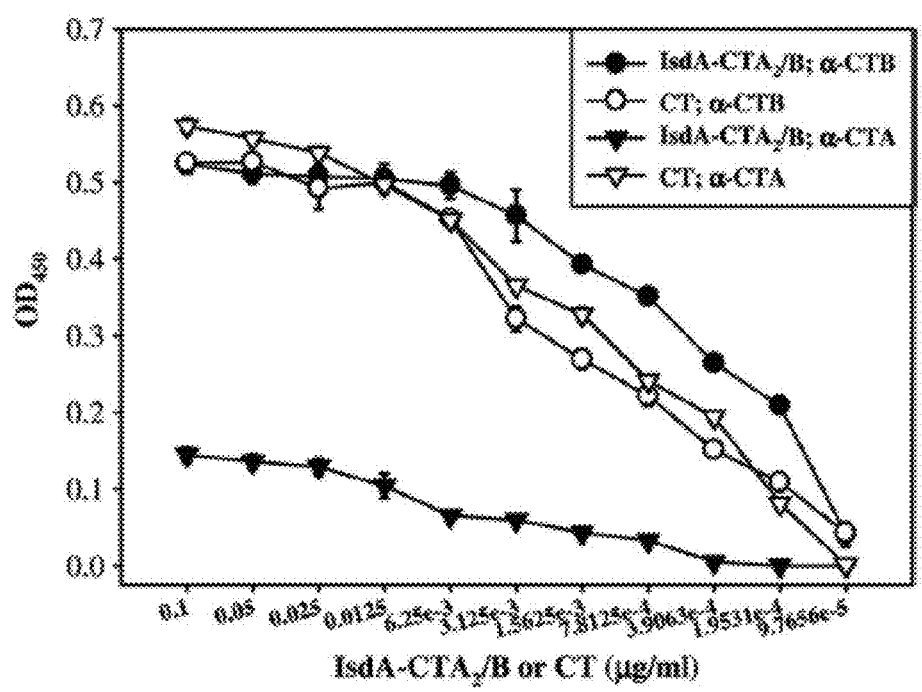
*FIG. 4*

CHOLERA TOXIN CHIMERA AND ITS USE AS A STAPH VACCINE

CROSS-REFERENCE TO RELATED APPLICATIONS

This present application is a continuation of U.S. patent application Ser. No. 15/910,783, filed Mar. 2, 2018, now U.S. Pat. No. 10,383,933, which is a continuation of U.S. patent application Ser. No. 14/456,090, filed Aug. 11, 2014, now U.S. Pat. No. 9,943,582 issued Apr. 17, 2018, which is a continuation of U.S. patent application Ser. No. 13/328,686, filed Dec. 16, 2011, now U.S. Pat. No. 8,834,898 issued Sep. 16, 2014, which is also a continuation of U.S. patent application ser. No. 13/896,854, filed May 17, 2013, now U.S. Pat. No. 8,911,748 issued Dec. 16, 2014.

This present application is also a continuation of U.S. patent application Ser. No. 13/896,854, filed May 17, 2013, now U.S. Pat. No. 8,911,748 issued Dec. 16, 2014, which is a continuation-in-part of U.S. patent application Ser. No. 13/328,686, filed Dec. 16, 2011, now U.S. Pat. No. 8,834,898 issued Sep. 16, 2014.

Each of these applications is hereby incorporated by reference.

FEDERAL FUNDING LEGEND

This invention was supported in part with government support under USDA CREES Seed Grant #2009-01778, 2008 WWAMI ITHS Small Project Grant #3872, 2012 ITHS Small Project Grant #5617, NIH Grant #P20 RR016454 from INBRE Program of the National Center for Research Resources, and a 2012 Idaho SBOE grant #IF-13-006 The Government has certain rights in the invention.

SEQUENCE LISTING

The instant application contains a Sequence Listing which has been submitted in ASCII format via EFS-Web and is hereby incorporated by reference in its entirety. Said ASCII copy, created on May 17, 2013, is named 083956-0028_SL.txt and is 53,242 bytes in size.

BACKGROUND

The present invention relates to infectious diseases and, more particularly, to chimeric protein vaccines and methods of use thereof in the treatment of Staphylococcus aureus.

Staphylococcus aureus (S. aureus) is a common cause of hospital-acquired infections and represents an important public health threat. S. aureus can cause nosocomial (hospital) and community-acquired infections including impetigo, cellulitis, food poisoning, toxic shock syndrome, invasive necrotizing pneumonia, and endocarditis. S. aureus is also the most common species of staphylococci to cause Staph infections. Currently, it is one of the top causes of infectious disease deaths in the United States.

S. aureus also causes mastitis, which is a major problem in dairy cows with considerable economic implications. For example, contagious mastitis in dairy cows is most commonly caused by S. aureus and is one of the most common diseases infecting dairy cattle in the United States. S. aureus causes a persistent, inflammatory reaction of the udder tissue that can lead to chronic infections that result in the cow being culled from the herd. Milk from cows with mastitis also typically has higher somatic cell count, which generally lowers the milk quality. It is estimated that mastitis may cost the dairy industry billions of dollars per year in economic losses.

A growing concern in the treatment of S. aureus is that the bacterium is often resistant to multiple antibiotics. Roughly half of the nosocomial isolates in the United States are methicillin-resistant S. aureus (MRSA). Methicillin-resistant S. aureus is also sometimes referred to as "multidrug-resistant" S. aureus or "oxacillin-resistant S. aureus." MRSA bacterium is generally resistant to beta-lactam antibiotics, which include the penicillins (e.g., methicillin, dicloxacillin, nafcillin, oxacillin, etc.) and cephalosporins. Currently, a vaccine that prevents staphylococcal disease is unavailable.

A possible approach for staphylococcal vaccine development is to target virulence factors such as toxins, enzymes, polysaccharide capsules, adhesive factors, and the like. A key to the possible vaccine approach may be that the anterior nares of humans are known to be an important niche for S. aureus. It is believed that nasal carriage is a major risk factor for invasive infection.

One potential S. aureus virulence factor is the iron-regulated surface determinant A (IsdA). IsdA is an S. aureus surface adhesin protein that may be immunogenic in certain organisms. IsdA can bind to human desquamated nasal epithelial cells and is believed to play a critical role in nasal colonization.

However, a major obstacle in vaccine development of S. aureus is the lack of immunostimulatory adjuvants that can function from mucosal surfaces. While certain toxins (e.g., cholera toxin and heat-labile toxin) have the ability to induce mucosal and systemic immune responses to co-administered antigens, these bacterial proteins are generally too toxic for human use.

SUMMARY OF THE INVENTION

The present invention relates to infectious diseases and, more particularly, to chimeric protein vaccines and methods of use thereof in the treatment of Staphylococcus aureus.

In some embodiments, the present invention provides methods of generating an immune response in a mammal comprising: administering to the mammal a composition comprising: a chimeric protein comprising at least one of: a portion of a cholera toxin, a portion of a heat-labile toxin, and a portion of a shiga toxin; and an antigen comprising at least one of: an antigenic material from S. aureus and an antigenic material from an S. aureus-specific polypeptide.

In other embodiments, the present invention provides a method of inducing an immune response in a cow comprising: administering to the cow a chimeric protein comprising: an adjuvant selected from the group consisting of: a portion of a cholera toxin, a portion of a heat-labile toxin, a portion of a shiga toxin, and any combination thereof; and an antigen selected from the group consisting of: an antigenic material from S. aureus, an antigenic material from a S. aureus-specific polypeptide, and any combination thereof.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modification, alteration, and equivalents in form and function, as will occur to those skilled in the art and having the benefit of this disclosure.

FIGS. 1A-1C show ribbon diagrams illustrating structures of cholera toxin, IsdA, and chimeric protein according to some embodiments.

FIG. 2 shows a diagram illustrating a plasmid that encodes a chimeric protein according to some embodiments.

FIGS. 3A-3B illustrate expression and purification of a chimeric protein according to some embodiments.

FIG. 4 shows a plot showing the results of a receptor binding affinity assay according to some embodiments.

FIGS. 5A-5D show confocal images of chimeric protein binding to Vero and DC2.4 cells stained with fluorescent dyes according to some embodiments.

FIG. 6 shows a plot showing in vivo systemic antibody response to chimeric protein according to some embodiments.

FIG. 7 shows a plot illustrating in vivo mucosal antibody response to chimeric protein according to some embodiments.

FIGS. 8A-8D show plots showing the results of flow cytometry experiments on the proliferation of T lymphocytes from mice immunized with chimeric protein according to some embodiments.

FIG. 9 shows a plot summarizing the flow cytometry results shown in FIGS. 8A-8D according to some embodiments.

FIG. 10 shows a plot showing the results of Resazurin assay of splenocytes from mice immunized with chimeric protein according to some embodiments.

FIG. 11 shows a plot showing IL-4 and IN-γ levels of antigen-stimulated splenocytes from mice immunized with chimeric protein according to some embodiments.

FIG. 12 shows a plot showing the results of IsdA-specific ELISA titrations of systemic antibody subtypes according to some embodiments.

FIGS. 13A-13B show a plot showing the effects of immune serum on *S. aureus* adhesion to human epithelial cells according to some embodiments.

FIG. 14A is a graph showing IsdA specific IgG serum titers in cows treated with IsdA-$CTA_2$/B (V) or control IsdA (C). FIG. 14B is a graph showing IsdA specific IgG milk titers in cows. FIG. 14C is a graph showing IsdA-specific IgA milk titers in cows. FIG. 14D is a graph showing IsdA-specific IgA nasal secretion titers in cows. FIG. 14E is a graph showing somatic cell counts in cows treated with IsdA-$CTA_2$/B or control IsdA.

FIG. 15A is an illustration of a plasmid pSKJ001 for expression of ClfA-$CTA_2$/B. FIG. 15B is an image of SDS-PAGE of the *S. aureus* ClfA$CTA_2$/B chimera (ClfA-$CTA_2$ approximately 37 kD, CTB equals 11.5 kD). FT=flow through, W1=wash 1, E=elution of D-galactose column.

FIG. 16A is an illustration of a plasmid pMPEZ001 for expression of IsdB-$CTA_2$/B. FIG. 16B is an image of SDS-PAGE of the *S. aureus* IsdB$CTA_2$/B chimera (IsdB-$CTA_2$ approximately 42 kD, CTB=11.5 kD). W1=wash 1, E=elution of D-galactose column.

DETAILED DESCRIPTION

The present invention relates to infectious diseases and, more particularly, to immunogenic compositions comprising chimeric proteins and methods of use thereof in the prevention of *Staphylococcus aureus.*

There are a number of advantages related to the present invention. The present invention provides compositions (in some embodiments, chimeric proteins) that may be useful as vaccines against various strains of *S. aureus* and related bacteria in various organisms (e.g., mammals such as humans, cows, etc.).

As used herein, the term "chimeric protein" generally refers to any protein comprised of a first amino acid sequence derived from a first source, bonded, covalently or non-covalently (e.g., hydrogen bonding, van der Waals force, hydrophobic interaction, etc.), to a second amino acid sequence derived from a second source, wherein the first and second source are not the same. A first source and a second source that are not the same can include two different biological entities, or two different proteins from the same biological entity, or a biological entity and a non-biological entity. A chimeric protein can include, for example, a protein derived from at least 2 different biological sources. A biological source can include any non-synthetically produced nucleic acid or amino acid sequence (e.g., a genomic or cDNA sequence, a plasmid or viral vector, a native virion or a mutant or analog, as further described herein, of any of the above). A synthetic source can include a protein or nucleic acid sequence produced chemically and not by a biological system (e.g., solid phase synthesis of amino acid sequences). A chimeric protein can also include a protein derived from at least 2 different synthetic sources or a protein derived from at least one biological source and at least one synthetic source. For the purposes of this disclosure, a chimeric protein may or may not be a single polypeptide (i.e., a fusion protein).

In some embodiments, the immunogenic compositions may be prophylactic and may be administered before the onset of *S. aureus* related infections. It is believed that the immunogenic compositions of the present invention can activate humoral responses, stimulate protection, and block the promotion of oral tolerance against *S. aureus*. Currently, there are no known vaccines that can prevent Staphylococcal infection.

The present invention provides compositions that comprise a first amino acid sequence derived from a suitable adjuvant source and a second amino acid sequence derived from a suitable antigen source. In some embodiments, the composition may have multiple functions. For example, the first amino acid sequence may act as an adjuvant while the second amino acid sequence may act as an antigen. As used herein, the term "amino acid sequence" does not necessarily imply a single polypeptide. In other words, the amino acid sequence derived from a suitable adjuvant source may not necessarily be confined to a single polypeptide. For example, a portion of the amino acid sequence may be in one polypeptide while the remaining portion of the amino acid sequence may reside in another polypeptide.

In some embodiments, the composition may be a single polypeptide (e.g., a fusion protein). In other embodiments, the composition may be assembled from two or more polypeptides. In certain embodiments having two or more polypeptides, one or more polypeptide may be chimeric. In certain embodiments, the two or more polypeptides may fold or assemble together within a suitable expression system (e.g., *E. coli*) or by any other suitable method (e.g., by the use of chaperone molecules).

The adjuvants typically used to construct the chimeric proteins of the present invention may be non-toxigenic or less toxigenic than full-length or non-chimeric toxins and yet retain their potent adjuvant characteristics. In some embodiments, the adjuvant may have been modified from a toxigenic adjuvant source with a modification that renders the adjuvant non-toxigenic or less toxigenic and likely suitable for mucosal surfaces. Such modifications may include, but are not limited to, mutation of amino acid, removal of toxigenic subunits, and the like.

Figure 5A:
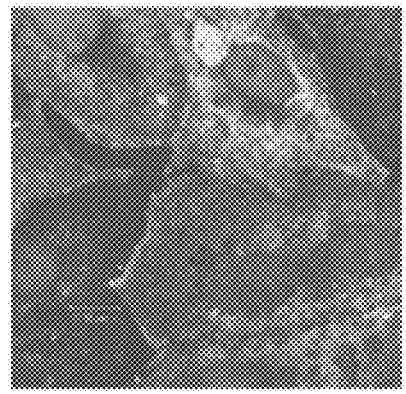
Figure 5C:
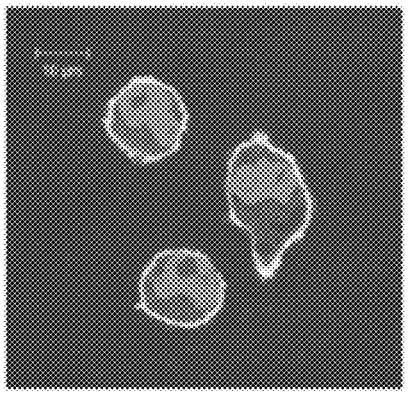
Figure 5B:
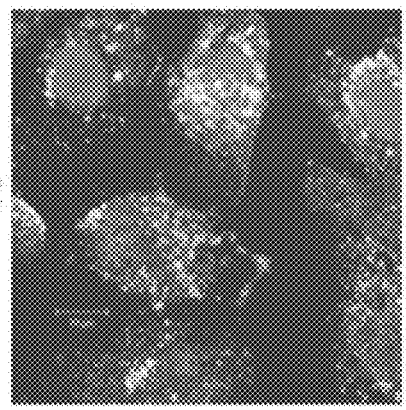
Figure 5D:
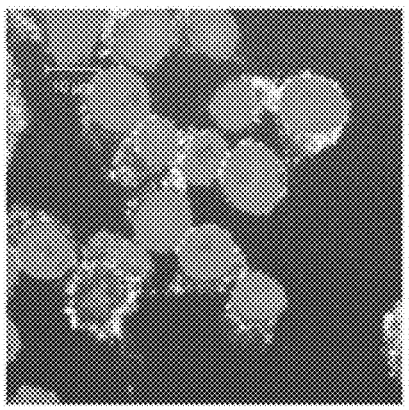
Figure 6:
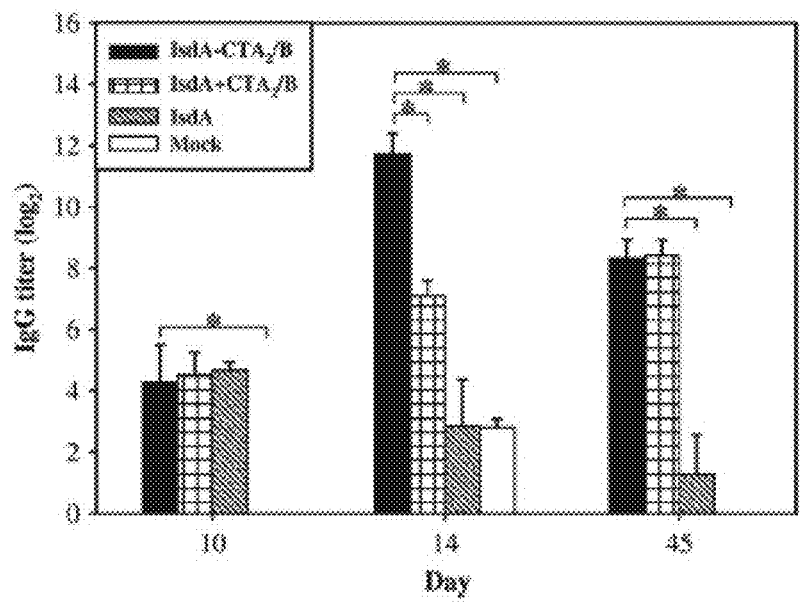
Figure 7:
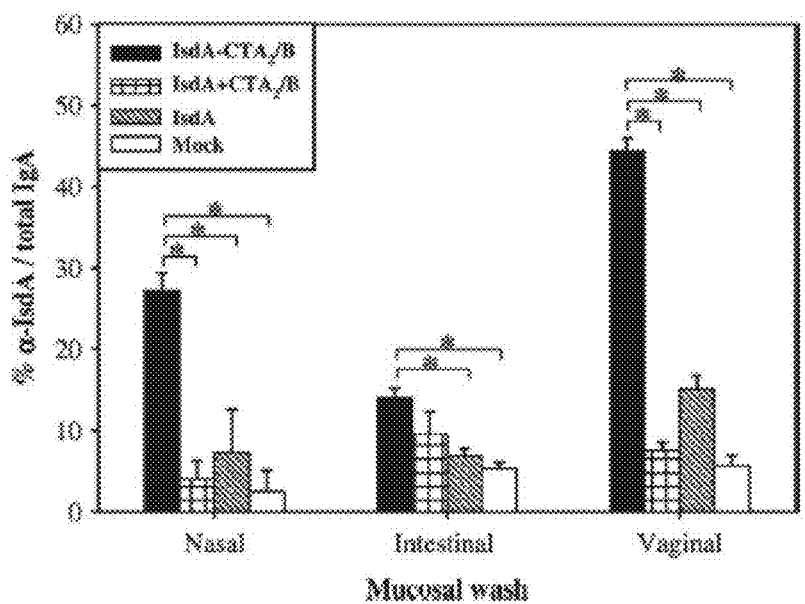
Figures 8A, 8C:
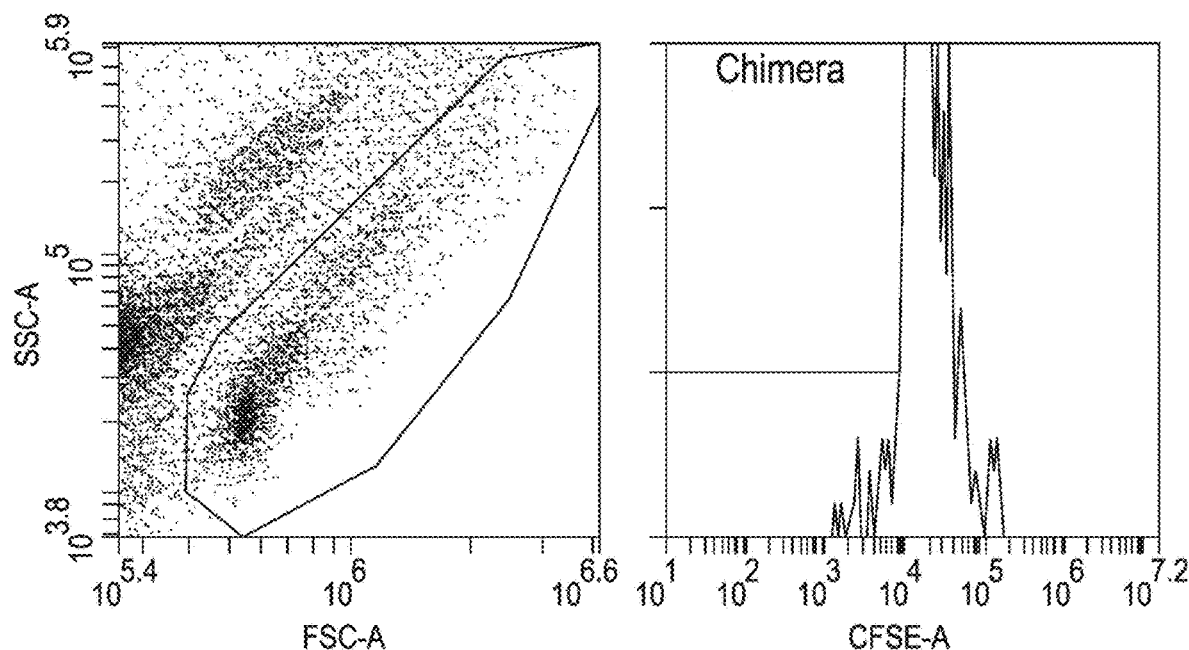
Figures 8B, 8D:
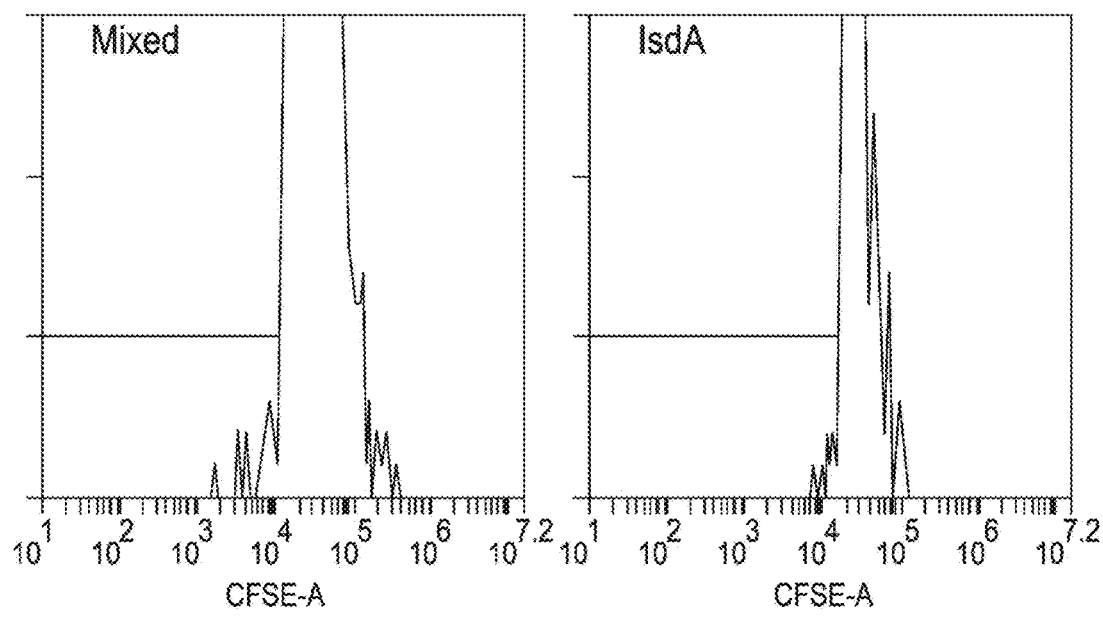

As used herein, an "adjuvant" generally refers to a pharmacological or an immunological agent that modifies the effect of other agents (e.g., drug or vaccine), while having few if any direct effects when given by itself. An immunological adjuvant is often included in vaccines to enhance the recipient's immune response to the antigen, while keeping the injection of foreign material to a minimum. For the purposes of this disclosure, an adjuvant may be linked covalently or non-covalently to the antigen.

While cholera toxin is an example of a potent adjuvant, it remains mostly unsuitable for use in humans. Specifically, there are safety concerns with the mucosal administration of cholera toxin and other similar toxins such as heat-labile toxin and shiga toxin. It is believed that such administration can redirect antigens to the central nervous system through GM1-dependent binding to olfactory epithelium. It has been previously difficult to separate the toxigenicity and adjuvanticity of cholera toxin, heat-labile toxin, and/or shiga toxin.

In some embodiments, the adjuvant source may be a toxin. The adjuvant may be coupled, assembled, folded, fused, or otherwise associated with an antigen to form a composition that further enhances the immunogenic effects of the antigen. Examples of suitable toxins include, but are not limited to, cholera toxin (CT), shiga toxin (ST1, ST2, etc.), heat-labile toxin (LT, LT-IIa, LT-IIb, etc.) from *E. coli*. In some preferred embodiments, the toxins are modified to be non-toxigenic while remaining potent immunostimulatory molecules that can bind to and target immune effector cells at mucosal site. It is believed that both shiga toxin and heat-labile toxin are structurally similar or analogous to cholera toxin.

In particular, cholera toxin is a protein secreted by the bacterium *Vibrio cholerae* and is generally responsible for the massive, watery diarrhea characteristic of cholera infection. Structurally, cholera toxin is an oligomeric complex made up of six protein subunits: a single copy of the A subunit (part A, enzymatic), and five copies of the B subunit (part B, receptor binding). The A subunit has two important segments: the A1 domain ($CTA_1$), which is toxigenic and the A2 domain ($CTA_2$), which forms an extended alpha helix that sits snugly in the central pore of the B subunit ring.

FIG. 1A shows a ribbon diagram of the cholera toxin crystal structure showing the $CTA_1$ domain (SEQ ID NO: 1) and connecting $CTA_2$ domain (SEQ ID NO:2), and the B subunit (SEQ ID NO: 3).

It is believed that cholera toxin immunomodulation may be involved in the activation of antigen-presenting cells, promotion of B-cell isotype switching, and upregulation of costimulatory and major histocompability complex (MHC) class II expression. Many of these responses result from the interaction of the cholera toxin B (CTB) subunit with the ganglioside GM1 receptor on effector cells, such as dendritic cells, that promote antigen uptake, presentation, and cellular activation. Thus, suitably modified non-toxigenic forms of cholera toxin by themselves may act as an antigen carrier and be highly immunostimulatory. Without being limited by theory, it is believed that heat-labile toxin and shiga toxin are structurally and functionally similar (e.g., adjuvanticity) to the cholera toxin.

For example, heat-labile toxin has an $A_1$ domain (SEQ ID NO: 7), $A_2$ domain (SEQ ID NO: 8), B domain (SEQ ID NO: 9) analogous to the $A_1$, $A_2$, and B domains of cholera toxin. An IsdA-$LTA_2$/B chimeric protein may have a sequence shown in SEQ ID NO: 10.

An antigen is generally any substance that causes the production of antibodies against it. An antigen may be a foreign substance from the environment or it may also be formed within the environment, such as bacterial toxins or tissue cells. Examples of a suitable antigen source include, but are not limited to, iron-regulated surface determinant A (IsdA), iron-regulated surface determinant B (IsdB), clumping factor A (ClfA), clumping factor B (ClfB), fibronectin-binding protein (FnBP), penicillin binding protein 2a (PBP2A), serine-aspartate rich fibrinogen sialoprotein binding protein (SdrE), and the like.

In particular, the N-terminal near iron transporter (NEAT) domain of IsdA is capable of binding to a broad spectrum of human ligands, including transferring heme, fibrinogen, fibronectin, and corneocyte envelope proteins to mediate adherence and dissemination of *S. aureus*. The C-terminal domain of IsdA defends *S. aureus* against human skin bactericidal fatty acids and antimicrobial peptides by making the cell surface hydrophilic.

FIG. 1B shows a ribbon diagram of IsdA antigen (SEQ ID NO: 4) that is replacing the toxigenic $CTA_1$ domain (SEQ ID NO: 1) to construct a chimeric protein that comprises an antigen and a non-toxigenic adjuvant. FIG. 1C shows a ribbon diagram of one preferred chimeric protein, IsdA-$CTA_2$/B (SEQ ID NO: 5).

Some embodiments provide compositions comprising: a chimeric protein comprising at least one of: a portion of a cholera toxin, a portion of a heat-labile toxin, and a portion of a shiga toxin; and an antigen comprising at least one of: an antigenic material from *S. aureus* and an antigenic material from a *S. aureus*-specific polypeptide.

In some embodiments, the composition is a fusion protein. In certain embodiments, the composition is a single polypeptide.

Some embodiments provide a chimeric protein comprising: an adjuvant and an antigen. The adjuvant may be selected from the group consisting of: a portion of a cholera toxin, a portion of a heat-labile toxin, a portion of a shiga toxin, and combinations thereof. The antigen may be selected from the group consisting of: an antigenic material from *S. aureus* (e.g., carbohydrates, peptides, etc.), an antigenic material from an *S. aureus*-specific polypeptide, and combinations thereof.

In some embodiments, the adjuvant is one of: $CTA_2$/B, $LTA_2$/B, or $STA_2$/B. In one or more embodiments, the adjuvant further includes at least one additional cholera toxin B subunit, heat-labile toxin B subunit (e.g., I or II), or shiga toxin B subunit (e.g., I or II). In one or more embodiments, the adjuvant further comprises at least one additional cholera toxin $A_2$ subunit, heat-labile toxin $A_2$ subunit (e.g., I or II), or shiga toxin $A_2$ subunit (e.g., I or II).

While some preferred embodiments of the domain and chimeric protein sequences have been provided, the present invention may be practiced using any number of alternative embodiments. For example, it is well known in the relevant arts that protein or polypeptide variants typically retain their function as long as they have sufficient sequence identity with their native sequences.

In some embodiments, the composition has at least about 80% sequence identity to SEQ ID NO: 5, 10, or 15. In some preferred embodiments, the composition has at least about 90% sequence identity to SEQ ID NO: 5, 10, or 15. In some preferred embodiments, the composition has at least about 95% sequence identity to SEQ ID NO: 5, 10, or 15. In certain embodiments, the antigen portion of the composition has at least about 80% sequence identity to SEQ ID NO: 4. In some preferred embodiments, the antigen portion of the composition has at least about 90% sequence identity to SEQ ID NO: 4. In some preferred embodiments, the antigen portion of the composition has at least about 95% sequence identity to SEQ ID NO: 4. In some embodiments, the composition is assembled from a first polypeptide and a second polypeptide that are non-covalently linked. In one or more of these embodiments, the first polypeptide has at least about 80% sequence identity to SEQ ID NO: 6, 11, or 16. In some preferred embodiments, the first polypeptide has at least about 90% sequence identity to SEQ ID NO: 6, 11, or 16. In some preferred embodiments, the first polypeptide has at least about 95% sequence identity to SEQ ID NO: 6, 11, or 16. In some embodiments, the second polypeptide has at least about 80% sequence identity to SEQ ID NO: 3, 9, or 14. In some preferred embodiments, the second polypeptide has at least about 90% sequence identity to SEQ ID NO: 3, 9, or 14. In some preferred embodiments, the second polypeptide has at least about 95% sequence identity to SEQ ID NO: 3, 9, or 14.

Generally, a chimeric protein will be comprised of a single $A_2$ subunit and a B subunit (from cholera toxin, heat-labile toxin, or shiga toxin). In some optional embodiments, the chimeric protein may further comprise at least one additional B subunit. In some optional embodiments, the B subunit may comprise five identical peptides. In some optional embodiments, the chimeric protein may further comprise at least one additional $A_2$ subunit. In some embodiments, the subunits may be linked by a disulfide bond. In some embodiments, the disulfide bond may be engineered. In some embodiments, the antigen has a disulfide bond with the adjuvant. In some embodiments, the antigen is associated non-covalently with the adjuvant.

In some embodiments, the antigen comprises a sequence that has at least about 80% sequence identity to iron-regulated surface determinant A (IsdA), iron-regulated surface determinant B (IsdB), clumping factor A (ClfA), clumping factor B (ClfB), fibronectin-binding protein (FnBP), fibronectin-binding protein (FnBP), penicillin binding protein 2a (PBP2A), or serine-aspartate rich fibrinogen sialoprotein binding protein (SdrE). In some preferred embodiments, the sequence identity is at least about 90%, or at least about 95%.

In some exemplary embodiments, the chimeric protein is IsdA-$CTA_2$/B (SEQ ID NO: 5). As used herein, "IsdA-$CTA_2$/B" generally refers to a chimeric protein that comprises an IsdA antigen domain, a $CTA_2$ subunit, and a CTB subunit. In some embodiments, each of the IsdA antigen domain (SEQ ID NO: 4), the $CTA_2$ domain (SEQ ID NO: 2) and the CTB domain (SEQ ID NO: 3) may be bonded covalently (e.g., peptide bonds, disulfide bonds, etc.) or non-covalently to at least one other domain. In some embodiments, the bond may be an engineered disulfide bond.

In some embodiments, the chimeric protein is IsdA-$LTA_2$/B (SEQ ID NO: 10). As used herein, "IsdA-$LTA_2$/B" generally refers to a chimeric protein that comprises an IsdA antigen domain, a $LTA_2$ subunit, and a LTB subunit. In some embodiments, each of the IsdA antigen domain (SEQ ID NO: 4), the $LTA_2$ subunit (SEQ ID NO: 8) and the CTB subunit (SEQ ID NO: 9) may be bonded covalently (e.g., peptide bonds, disulfide bonds, etc.) or non-covalently to at least one other domain. In some embodiments, the bond may be an engineered disulfide bond.

In some embodiments, the chimeric protein is IsdA-$STA_2$/B (SEQ ID NO: 15). As used herein, "IsdA-$STA_2$/B" generally refers to a chimeric protein that comprises an IsdA antigen domain, a $STA_2$ subunit, and a STB subunit. In some embodiments, each of the IsdA antigen domain (SEQ ID NO: 4), the $STA_2$ subunit (SEQ ID NO: 13) and the STB subunit (SEQ ID NO: 14) may be bonded covalently (e.g., peptide bonds, disulfide bonds, etc.) or non-covalently to at least one other domain. In some embodiments, the bond may be an engineered disulfide bond.

In some embodiments, the chimeric protein is IsdB-$CTA_2$/B (amino acids 24-367 of SEQ ID NO: 22). As used herein, "IsdB-$CTA_2$/B" generally refers to a chimeric protein that comprises an IsdB antigen domain, a $CTA_2$ subunit, and a CTB subunit. In some embodiments, each of the IsdB antigen domain (amino acids 42-338 of SEQ ID NO: 23), the $CTA_2$ subunit (SEQ ID NO: 2) and the CTB subunit (SEQ ID NO: 3) may be bonded covalently (e.g., peptide bonds, disulfide bonds, etc.) or non-covalently to at least one other domain. In some embodiments, the bond may be an engineered disulfide bond.

In some embodiments, the chimeric protein is ClfA-$CTA_2$/B (amino acids 24-347 of SEQ ID NO: 24). As used herein, "ClfA-$CTA_2$/B" generally refers to a chimeric protein that comprises a ClfA antigen domain, a $CTA_2$ subunit, and a CTB subunit. In some embodiments, each of the ClfA antigen domain (amino acids 287-559 of SEQ ID NO: 25), the $CTA_2$ subunit (SEQ ID NO: 2) and the CTB subunit (SEQ ID NO: 3) may be bonded covalently (e.g., peptide bonds, disulfide bonds, etc.) or non-covalently to at least one other domain. In some embodiments, the bond may be an engineered disulfide bond.

In some embodiments, the chimeric protein may further comprise modifications that enhance at least one of: solubility of the chimeric protein, specificity for S. aureus, specificity for GM1, expression of the chimeric protein, and immunogenicity of the chimeric protein.

Some embodiments provide methods for generating an immune response in a mammal comprising: administering to the mammal a composition (e.g., chimeric protein) according to one or more embodiments described herein.

In some embodiments, the mammal is selected from the group consisting of: a human, a cow, a dog, a cat, and a horse.

In some embodiments, the administration of the composition is by intranasal administration, oral administration, intramuscular administration, peritoneal administration, sublingual administration, transcutaneous administration, subcutaneous administration, intravaginal administration, intramammary administration or intrarectal administration. The administered dosage of the composition may generally be an amount suitable to elicit the desired immune response. In some embodiments, the administering to the mammal comprises: administering the composition to at least one cell from the mammal in vitro or in vivo.

Some embodiments provide methods for inducing an immune response in a cow comprising: administering to the cow, a chimeric protein according to one or more embodiments described herein.

To facilitate a better understanding of the present invention, the following examples of preferred embodiments are given. In no way should the following examples be read to limit, or to define, the scope of the invention.

EXAMPLE 1

To direct the IsdA-$CTA_2$ and CTB peptides of the chimera to the E. coli periplasm for proper assembly, pBA001 (FIG. 2) was constructed from pARLDR19, which utilizes the E. coli LTIIb N-terminal leader sequence. Induction of pBA001 and purification from the periplasm of E. coli resulted in efficient IsdA-$CTA_2$/B production (3 to 4 mg from 1 liter of starting culture). SDS-PAGE analysis of the purification of IsdA-$CTA_2$/B and immunoblotting using antibodies against CTA and CTB (FIG. 3A) confirm that IsdA-$CTA_2$ (~38 kDa) was copurified with CTB (~11 kDa) on D-galactose agarose, which is indicative of proper chimera folding. Referring to FIG. 3A, the SDS-PAGE analysis shows flowthrough (FT), washes (W1 and W2) and elution (E) of IsdA-CTA$_2$/B from D-galactose affinity purification and anti-CTA/B Western blot of purified IsdA-CTA$_2$/B (~38 and 11 kDA).

IsdA alone was also purified using a six-histidine tag (SEQ ID NO: 26). FIG. 3B shows an SDS-polyacrylamide gel of all resulting proteins used in animal studies, as well as immunoblotting of purified IsdA with anti-His6 ("His6" disclosed as SEQ ID NO: 26) (~37 kDa): ISdA-$CTA_2$/B (G1), IsdA plus $CTA_2$/B mixed (G2), and IsdA (G3).

The following protocol was followed in order to obtain the chimeric proteins.

MRSA252 strain was used for IsdA isolation. MRSA USA300 (pvl mutant) strain was used in adhesion assays. *E. coli* TE1, a ΔendA derivative of TX1, and BL21(DE3)/pLysS strains were used for protein expression. All bacterial strains were cultured using Luria-Bertani (LB) agar or broth at 37° C. with chloramphenicol (35 μg/ml), ampicillin (100 μg/ml), and/or kanamycin (50 μg/ml).

To construct pBA001 plasmid (FIG. 2) for the expression of IsdA-$CTA_2$/B, IsdA was PCR amplified from MRSA252 with primers that add 5' SphI GCTACTGGCATGCG-GCAACAGAAGCTACGAAC (SEQ ID NO: 17) and 3' ClaI GTGCATGATCGATTTTGGTAATTCTTTAGC (SEQ ID NO: 18) sites (in boldface) and cloned into pARLDR19 between the LTIIb leader sequence and $CTXA_2$. CTB was also expressed from this vector. To make His6-IsdA IsdA ("His6" disclosed as SEQ ID NO: 26), IsdA was amplified from MRSA252 with primers that add 5' BamHI GCTACTGGATCCGCGGCAACAGAAGCTACGAAC (SEQ ID NO: 19) or GTGCATAAGCTTTCAAGTTTTTG-GTAATTCTTTAGC (SEQ ID NO: 20) and 3' HindIII GTG-CATGATCGATTTTGGTAATTCTTTAGC (SEQ ID NO: 21) sites (in boldface) and cloned into pTrcHisA (Invitrogen, Carlsbad, Calif.) or pET-40b+, yielding pBA009A and pBA015. pARLDR19 was used to express $CTA_2$/B for the mixed preparation. Plasmids were transformed into *E. coli* TE1 (pBA001, pBA009A, and pARLDR19) or BL21(DE3)/pLysS (pBA015) and sequenced.

To express IsdA-$CTA_2$/B and $CTA_2$/B, cultures with pBA001 or pARLDR19 were grown to an optical density at 600 nm (OD600) of 0.9 and induced for 15 h with 0.2% L-arabinose. Proteins were purified from the periplasmic extract using immobilized D-galactose. For mock cultures, *E. coli* TE1 without plasmid was induced, and the periplasmic extract was purified. IsdA was isolated from the cytosol of cultures containing pBA009A and purified by cobalt affinity chromatography under denaturing conditions. IsdA was also purified from periplasmic extracts of cultures containing pBA015 over Talon resin under native conditions. All proteins were dialyzed against phosphate-buffered saline (PBS), reduced to <0.125 endotoxin units (EU)/ml lipopolysaccharide by passage through an endotoxin removal column, and quantified by bicinchoninic acid assay prior to the addition of 5% glycerol.

Proteins resolved by SDS-12% PAGE were stained with COOMASSIE or transferred to nitrocellulose membranes. Membranes were blocked overnight with 5% skim milk in PBS plus 0.05% TWEEN 20 (PBS-T), incubated with polyclonal anti-CTA (1:2,500) and anti-CTB (1:5,000) or anti-His6 ("His6" disclosed as SEQ ID NO: 26) (1:2,500), followed by horseradish peroxidase (HRP)-conjugated anti-rabbit IgG (1:5,000) and developed with IMMOBILON WESTERN HRP SUBSTRATE commercially available from Millipore, Billerica, MA.

EXAMPLE 2

To compare the receptor binding affinity of purified IsdA-$CTA_2$/B chimera with native CT, ganglioside GM1 ELISA assays using anti-CTA and anti-CTB antibodies were performed.

GM1 enzyme-linked immunosorbent assays (ELISA) were performed by coating microtiter plates with 0.15 μM GM1 for 15 h at 20° C., blocking with 10% bovine serum albumin, and incubating with IsdA-$CTA_2$/B or CT for 1 h at 37° C. Ganglioside GM1 is found ubiquitously on mammalian cells and acts as the site of binding for both cholera toxin and heat-labile toxin. Plates were washed with PBS-T and incubated with anti-CTA (1:2,000) or anti-CTB (1:5,000) followed by HRP-conjugated anti-rabbit IgG, both for 1 h at 37° C. The reaction was developed with o-phenylenediamine dihydrochloride ($A_{450}$).

The ELISA results indicate that the B subunit of IsdA-$CTA_2$/B has GM1 binding affinity similar to that of CT (FIG. 4). Low anti-CTA response from IsdA-$CTA_2$/B was an expected result from this fusion that contains only 46 bp of full-length CTA.

Confocal microscopy was used to further confirm receptor binding and internalization of IsdA-$CTA_2$/B into epithelial and dendritic cells (DC) in vitro. Immune effector cells, such as dendritic cells, have a uniquely high affinity for CT and non-toxigenic CTB. FIGS. 5A-5D show anti-CT FITC-labeled IsdA-$CTA_2$/B bound to the surface of cells (Vero epithelial cells in FIG. 5A-5B; DC cells in FIG. 5C-5D) at 4° C. and internalization after 45 min at 37° C., indicating that, at a minimum, the CTB subunit of the chimera were efficiently imported into the cell. These images obtained using polyclonal anti-CT and anti-rabbit-FITC with DAPI suggest that IsdA-$CTA_2$/B was binding and transporting into Vero and DC2.4 cells. Cells were incubated with IsdA-$CTA_2$/B for 45 minutes at 4° C. to inhibit, or at 37° C. to promote cellular uptake.

EXAMPLE 3

The chimeric proteins were tested for their specific humoral response.

BALB/c mice were mock immunized or immunized intranasally with IsdA-$CTA_2$/B, IsdA plus $CTA_2$/B mixed, or IsdA on day 0 and boosted on day 10 (Table 1 below). FIG. 6 shows systemic antibody response to IsdA-$CTA_2$/B in vivo. Referring to FIG. 6, sera collected on days 0, 10, 14, and 45 were pooled by treatment group at each time point and tested for recognition of IsdA by IgG ELISA. IsdA-specific serum IgG endpoint titers from mice immunized with IsdA-$CTA_2$/B were significantly higher than those of mock-immunized mice on day 10, than those of all control groups on day 14, and than those of mice immunized with IsdA alone and mock-immunized mice on day 45. As used herein, "*" denotes statistical significance (P<0.05) between mice immunized with IsdA-$CTA_2$/B versus controls. Nasal, intestinal, and vaginal washes were collected on day 45, pooled by treatment group, and tested for recognition of IsdA by IgA ELISA.

FIG. 7 shows mucosal antibody response to IsdA-$CTA_2$/B in vivo. Referring to FIG. 7, the percentage of IsdA-IgA out of total IgA was significantly higher in nasal and vaginal washes from mice immunized with IsdA-$CTA_2$/B than from mock-immunized mice, mice immunized with IsdA plus $CTA_2$/B, or mice immunized with IsdA alone. In addition, intestinal IsdA-IgA was significantly higher in IsdA-$CTA_2$/B-immunized mice than in IsdA- and mock-immunized mice (FIG. 7). Together, these results suggest that IsdA specific systemic and mucosal humoral immunity can be stimulated after intranasal vaccination with the IsdA-CTA$_2$/B chimera.

TABLE 1

Immunization Strategy.

| Antigen/ adjuvant | Dose per vaccination (µg) | n[b] | Days of intranasal vaccination | Days of sampling | |
|---|---|---|---|---|---|
| | | | | Sera | Mucosal secretions and spleen (n) |
| IsdA-CTA$_2$/B chimera | 50 | 8 | 0, 10 | 0, 10, 14, 45 | 14 (2), 45 (6) |
| IsdA + CTA$_2$/B | 17 + 33[a] | 8 | 0, 10 | 0, 10, 14, 45 | 14 (2), 45 (6) |
| IsdA | 17 | 8 | 0, 10 | 0, 10, 14, 45 | 14 (2), 45 (6) |
| Mock | NA[c] | 8 | 0, 10 | 0, 10, 14, 45 | 14 (2), 45 (6) |

[a]Concentrations are according to equimolar to equimolar amounts of IsdA
[b]n, number of mice
[c]NA, not applicable

EXAMPLE 4

Figure 9:
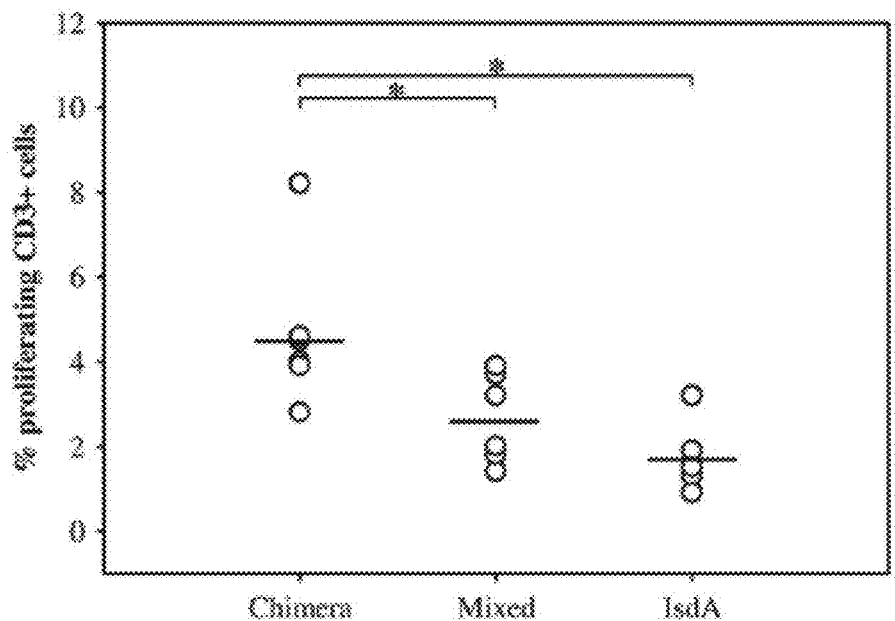

Cellular proliferation of IsdA-stimulated splenocytes was assessed using flow cytometry and a resazurin-based fluorescent dye assay. CFSE-based flow cytometric results suggest that day 45 splenocytes derived from mice immunized with IsdA-CTA$_2$/B showed significant proliferation of IsdA-specific CD3+T lymphocytes compared with mixed and IsdA control groups (FIGS. 8A-8D and 9). Referring to FIGS. 8A-8D, CFSE-labeled splenocytes were cultured in vitro for 84 h with IsdA and stained with anti-CD3-PE-Cy5. Referring to FIG. 9, percent proliferation of IsdA-specific CD3+ T lymphocytes from individual mice on day 45 was determined by flow cytometry. Mock samples contained low numbers of CD3+ T lymphocytes.

Figure 10:
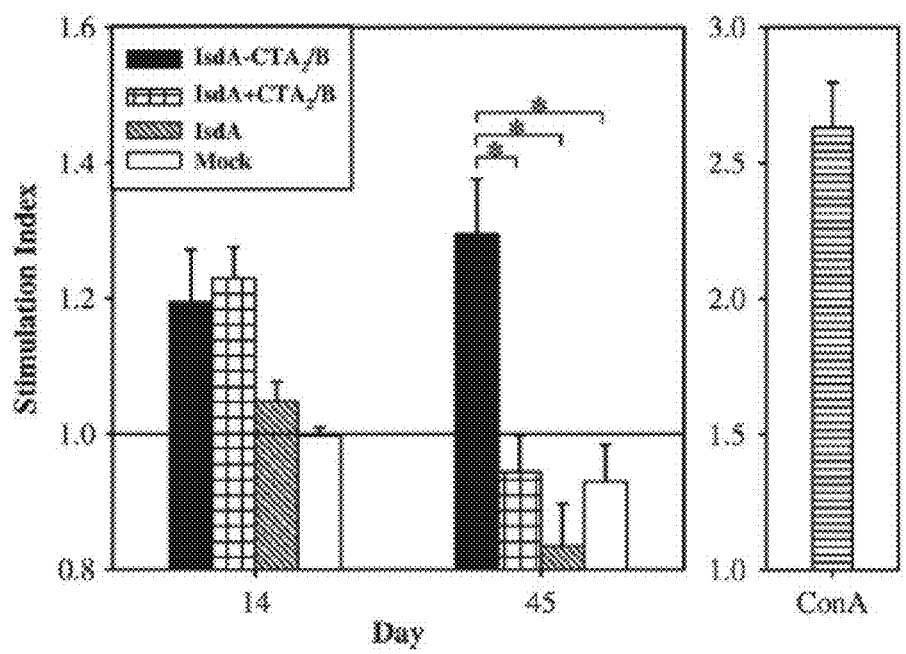

FIG. 10 shows the result of a resazurin assay of splenocytes from days 14 and 45 cultured in vitro for 84 h with IsdA. The resazurin assays revealed that in vitro stimulation of splenocytes from IsdA-CTA$_2$/B-immunized mice induced significant proliferation compared with IsdA plus CTA$_2$/B, IsdA, and mock groups on day 45 (FIG. 10). With the low sample size (n=2 per group) on day 14, no significance was observed between groups. Error bars are based on n=2 (day 14) or n=6 (day 45). Stimulation was observed for the positive control, ConA. These results suggest that intranasal administration of IsdA-CTA$_2$/B can induce a cellular activation response.

EXAMPLE 5

Figure 11:
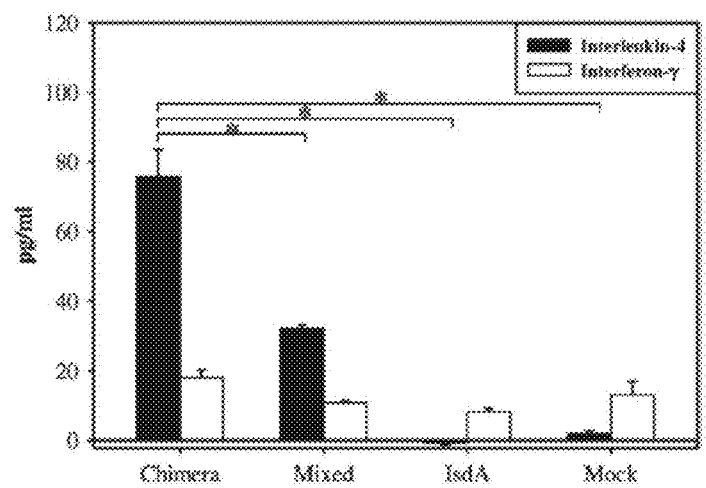

The levels of IL-4 and IFN-γ in supernatants of splenocytes stimulated with IsdA in vitro were determined by ELISA. Referring to FIG. 11, IL-4 and IFN-γ levels in culture supernatants from splenocytes, pooled by immunization group (n=6), were stimulated in vitro for 84 h with IsdA and measured by ELISA. The splenocytes obtained from mice immunized with IsdA-CTA$_2$/B secreted high levels of IL-4, and these levels were significantly higher than levels of all controls (FIG. 11). Although the level of IFN-γ was slightly higher in IsdA-CTA$_2$/B-immune splenocytes, low levels of IFN-γ, near the detection limit for the assay, were found in all groups (FIG. 11).

Figure 12:
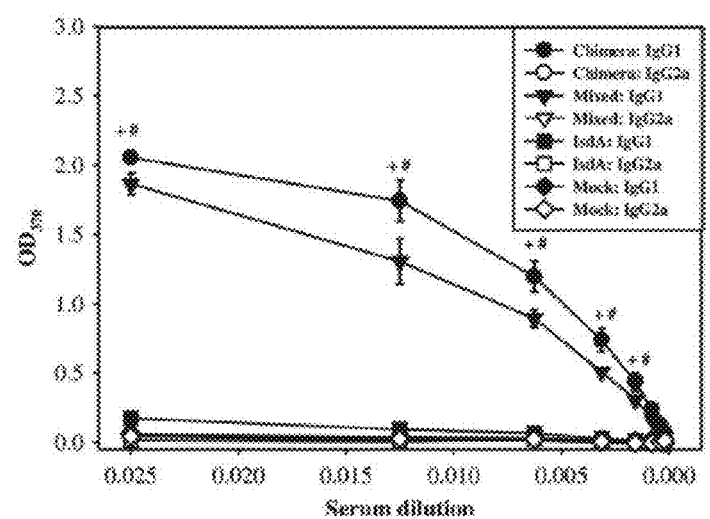

FIG. 12 shows IsdA-specific IgG1 and IgG2a ELISA titrations from day 45 sera pooled by immunization group (n=6). Titrations of IgG1 and IgG2a revealed that immunization with IsdA-CTA$_2$/B drove isotype switching primarily to the IgG1 subclass although minute IgG2a levels were also detected. These results suggest that immunization with IsdA-CTA$_2$/B promotes a Th2-type immune response.

EXAMPLE 6

Figure 13A:
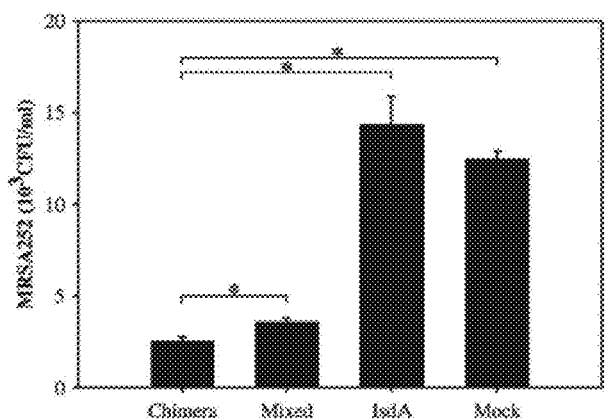
Figure 13B:
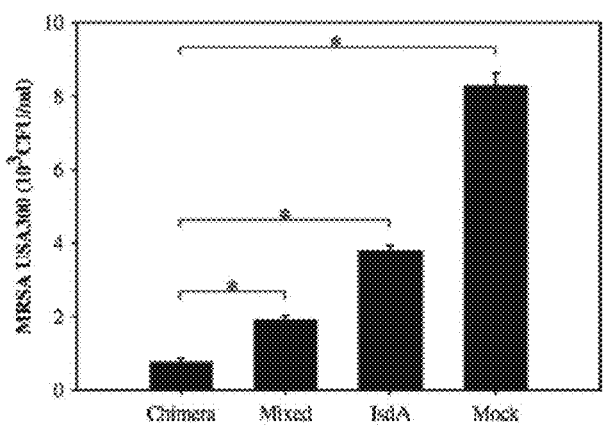
Figure 14A:
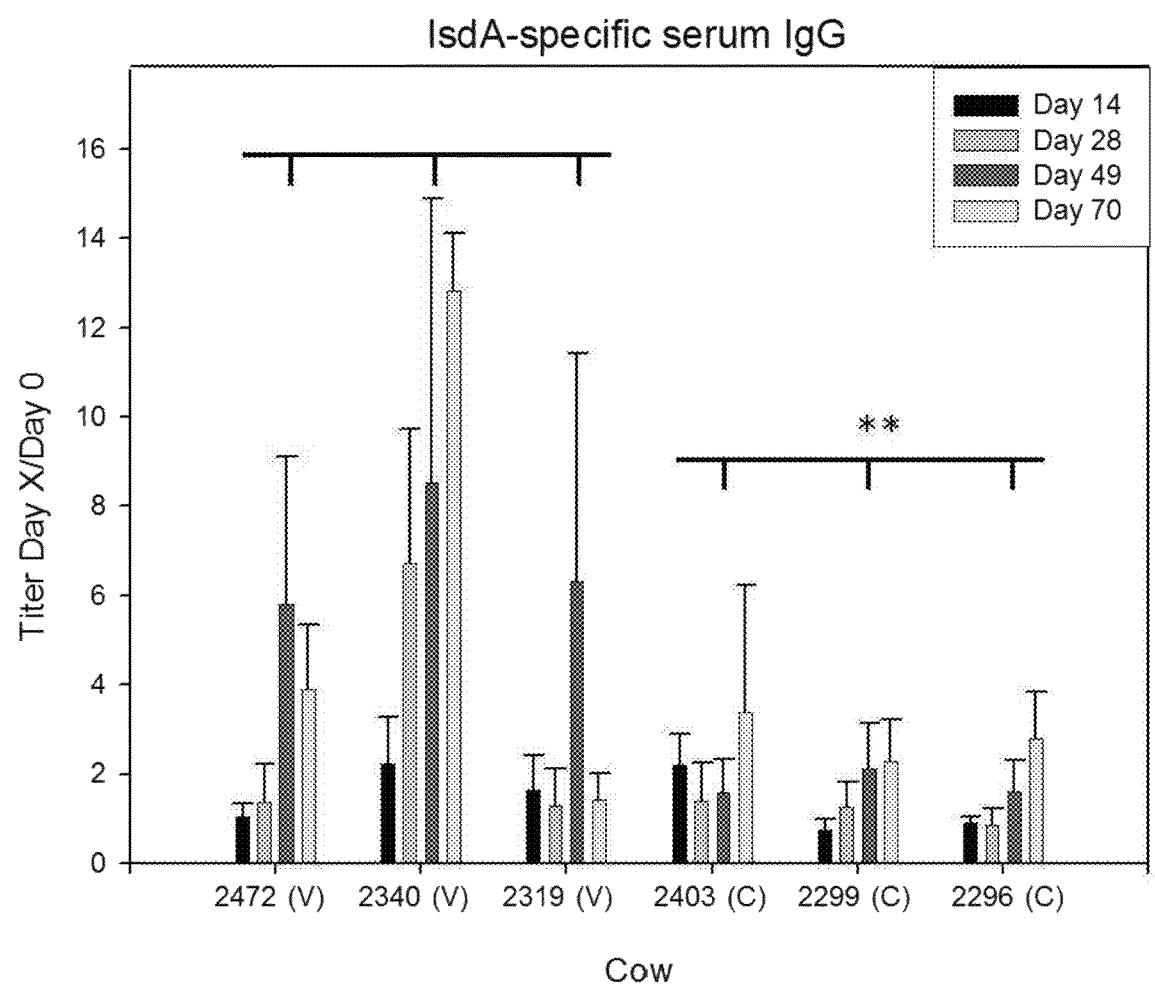
Figure 14B:
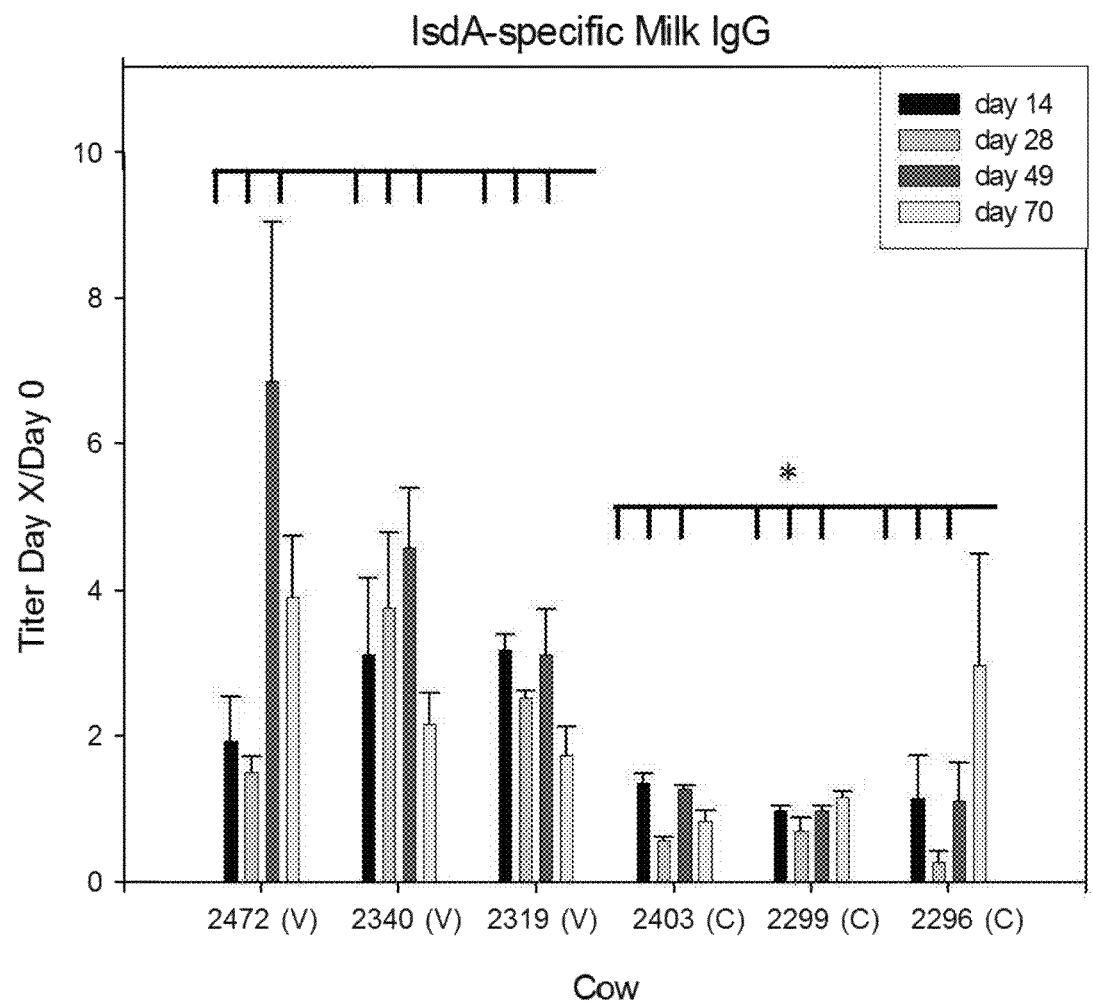
Figure 14C:
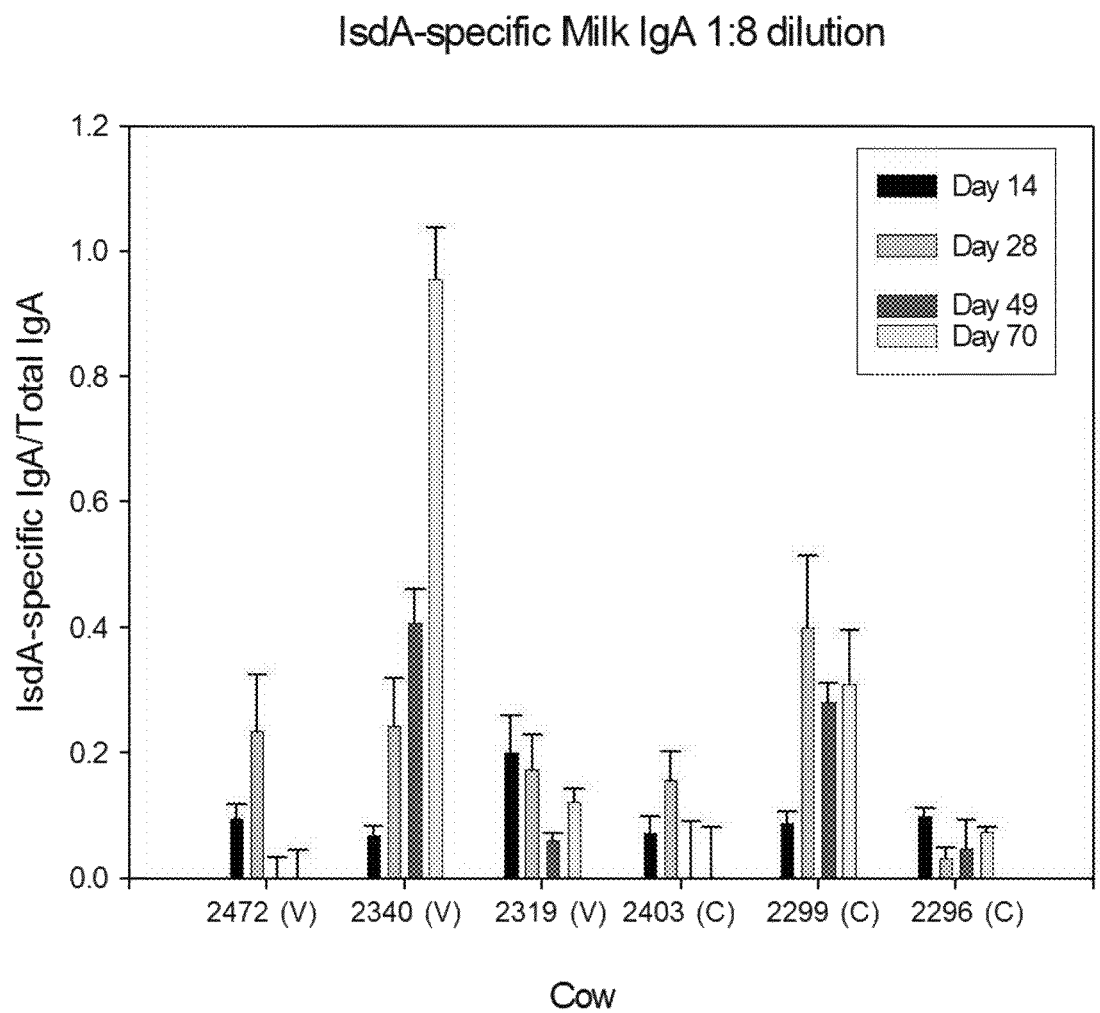
Figure 14D:
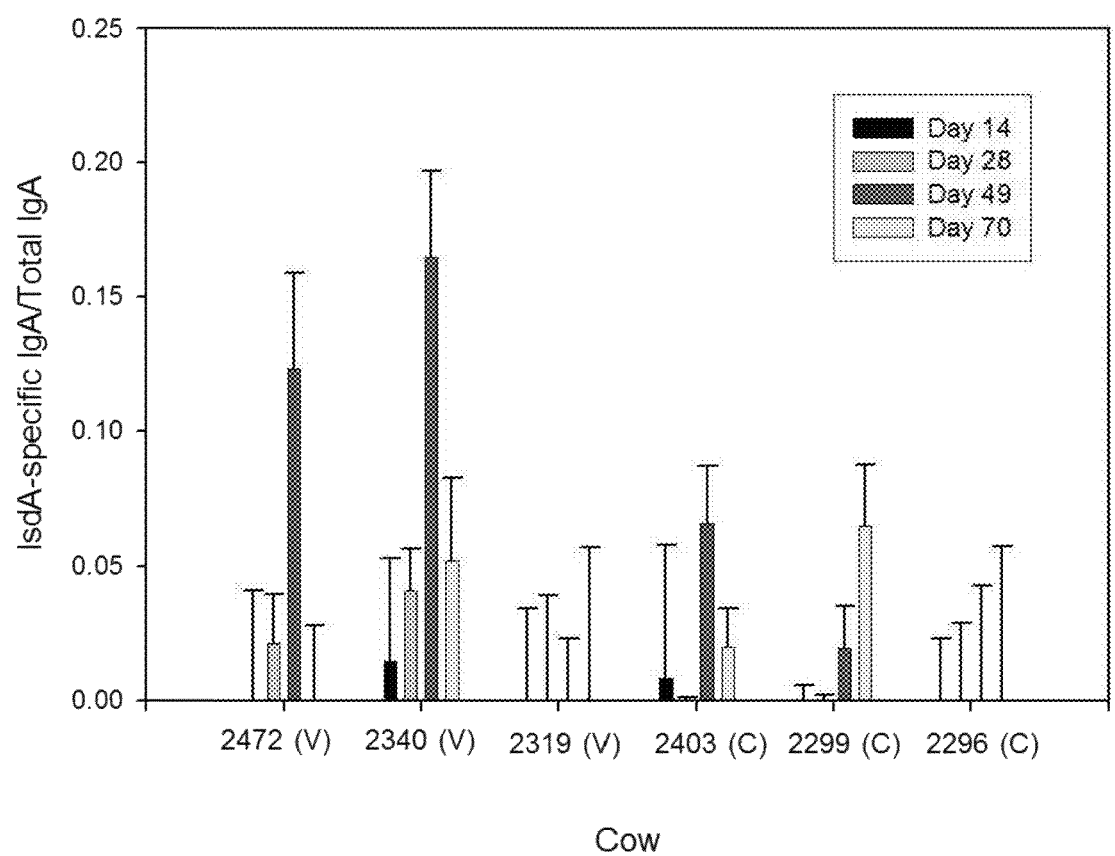
Figure 14E:
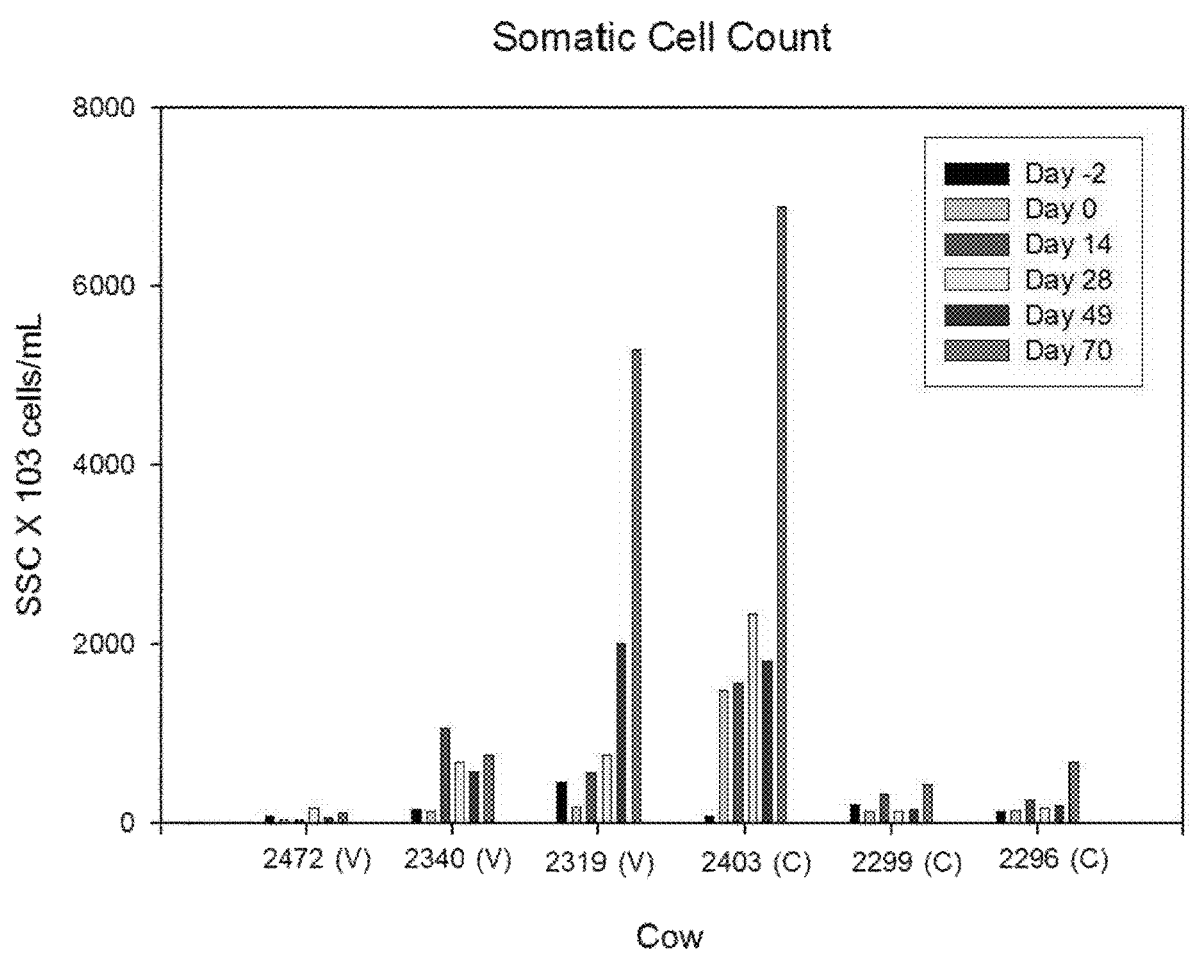

Pooled sera from commonly immunized mice were used to investigate the ability of immune serum to functionally block adherence of S. aureus to human epithelial cells (HeLa). FIGS. 13A-13B show the effect of immune serum on S. aureus adhesion to human epithelial cells in vitro. Referring to FIG. 13A, sera (1:100; day 45) was pooled by immunization group and incubated with MRSA252 (5×10$^7$ CFU) for 1 h at 37° C. and then added to confluent HeLa cells. After washing and lysis, the number of internalized and cell-bound bacteria was enumerated. Preincubation of the S. aureus strain used for vaccination (MRSA252) with day 45 sera from IsdA-CTA$_2$/B-immunized mice significantly reduced bacterial adhesion to epithelial cells compared to all control groups (FIG. 13A).

FIG. 13B shows the result of similar tests performed with MRSA USA300 (5×10$^9$ CFU). Referring to FIG. 13B, there was a significant reduction in bacterial adhesion to human epithelial cells after a different strain of S. aureus (MRSA USA300) was preincubated with day 45 sera from mice immunized with IsdA-CTA$_2$/B (FIG. 13B).

These examples suggest that the chimeric proteins of the present invention can bind and transport into epithelial and dendritic cells as consistent with the uptake of CT involving retrograde movement to the perinuclear domain of the Golgi apparatus and endoplastmic reticulum. It is believed that the ability of the chimeric proteins to bind to GM1 and trigger internalization leads to the activation of immune effector cells by the CTB subunit and promotes antigen presentation on MHC molecules.

Moreover, the ELISAs of IsdA-specific responses from the sera and nasal, intestinal, and vaginal fluids of intranasally immunized mice verifies that the chimeric proteins can induce antigen-specific systemic and mucosal immunity in mice. As expected, IgG titers were highest on day 14 after the boost and began to diminish by day 45.

These results also suggest the characteristic ability of CT to induce systemic IgG to antigens co-administered with CT at mucosal sites. The presence of IsdA-specific IgA in nasal, intestinal, and vaginal fluids after intranasal immunization with IsdA-CTA$_2$/B suggests that IgA blasts migrated from the nasal-associated lymphoid tissue into distal mucosal effector sites in the nasal passage and gastrointestinal and genital tracts. Thus, it is believed that CT and CT derivatives promote more of a Th2-type response, which is typically characterized by secretion of IL-4 leading to induction of antibody class switching to non-complement-activating IgG1. In vitro functional assays of antibodies revealed a significant reduction in internalized and cell-bound bacteria on human epithelial cells after preincubation of IsdA-CTA$_2$/B immune serum with the S. aureus isolate used for vaccination, MRSA252. Additionally, antibodies were able to prevent adhesion of MRSA USA300.

IsdA from MRSA252 and MRSA USA300 has 92% amino acid identity with the majority of differences present within the C terminus, which suggests that antibodies against IsdA are functional in vitro and may protect against multiple serotypes in vivo.

The results also suggest that the humoral and cellular responses induced by IsdA-CTA$_2$/B are superior to those stimulated by a mixed preparation of antigen and adjuvant (IsdA plus CTA$_2$/B). Thus, the structure of the IsdA-CTA$_2$/B chimera is optimal for the induction of antigen-specific humoral responses and potentially for presentation on MHC molecules.

EXAMPLE 7

Figure 15A:
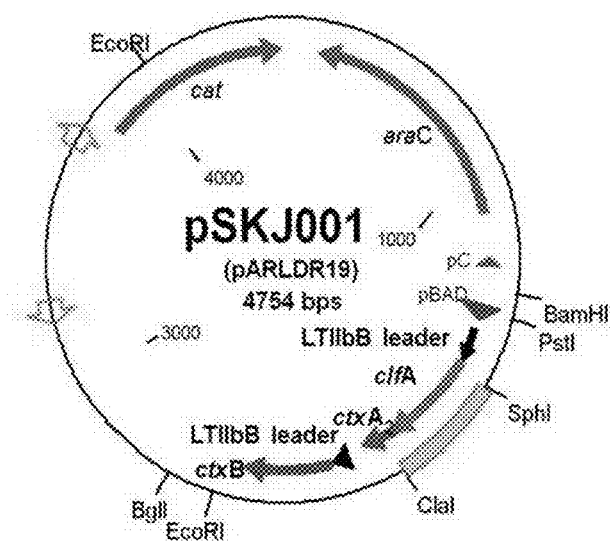
Figure 15B:
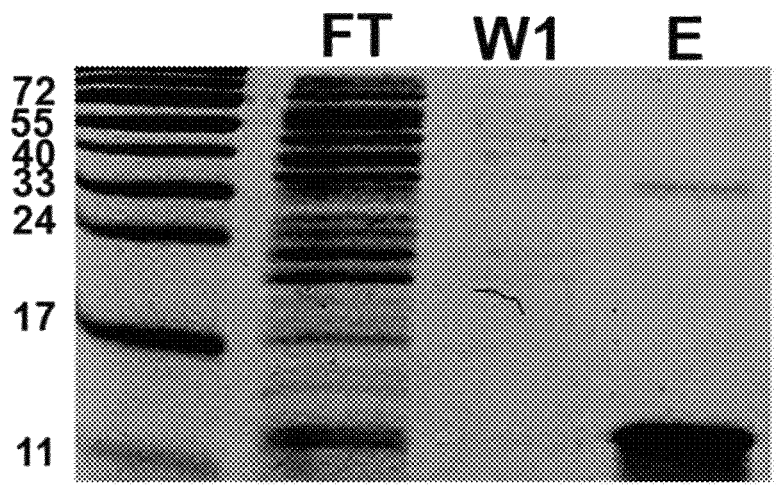

To direct the ClfA-CTA$_2$ and CTB peptides of the chimera to the E. coli periplasm for proper assembly, pSKJ001 (FIG. 15A) was constructed from pARLDR19, which utilizes the E. coli LTIIb N-terminal leader sequence. SDS-PAGE analysis of the purification of ClfA-CTA$_2$/B confirms that ClfA-CTA$_2$ (~37 kDa) was copurified with CTB (11.5 kDa) on D-galactose agarose, which is indicative of proper chimera folding. Referring to FIG. 15B, the SDS-PAGE analysis shows flowthrough (FT), wash 1 (W1) and elution (E) of ClfA-CTA$_2$/B from D-galactose affinity purification.

Figure 16A:
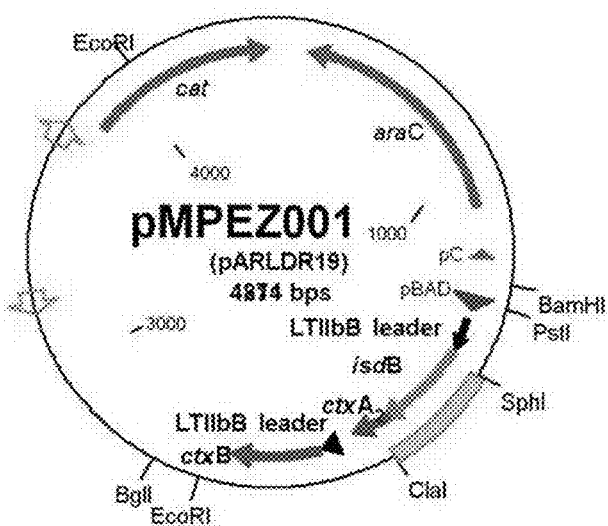
Figure 16B:
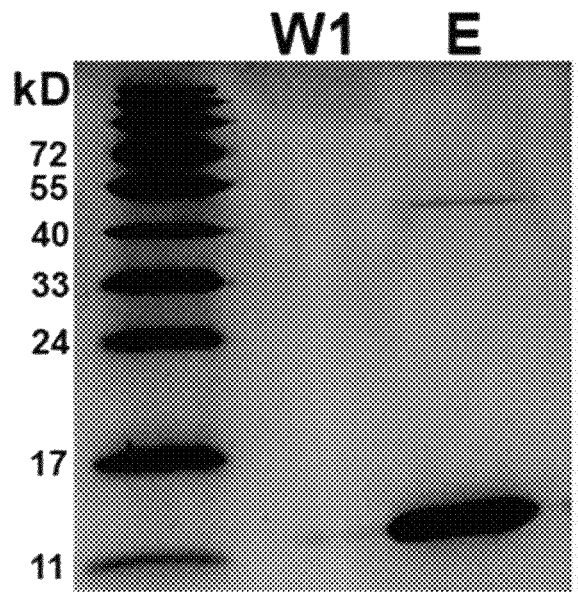

To direct the IsdB-CTA$_2$ and CTB peptides of the chimera to the E. coli periplasm for proper assembly, pSKJ001 (FIG. 16A) was constructed from pARLDR19, which utilizes the E. coli LTIIb N-terminal leader sequence. SDS-PAGE analysis of the purification of IsdB-CTA$_2$/B confirms that IsdB-CTA$_2$ (~42 kDa) was copurified with CTB (11.5 kDa) on D-galactose agarose, which is indicative of proper chimera folding. Referring to FIG. 16B, the SDS-PAGE analysis shows flowthrough (FT), wash 1 (W1) and elution (E) of IsdB-CTA$_2$/B from D-galactose affinity purification.

EXAMPLE 8

Milk anti-IsdA IgA titer levels were measured in cows treated with a chimeric protein according to one or more embodiments of the present invention. Six (2472, 2340, 2319, 2403, 2299, 2296) clinically healthy Holstein dairy cows were vaccinated intranasally on day 0 with 300 µg of IsdA-CTA$_2$/B chimera (cows 2472, 2340, 2319) or an equivalent concentration of IsdA alone (cows 2403, 2299, 2296). Cows were boosted on day 14 with the same concentration. Milk was collected on days 0, 14 and 28 and analyzed by IsdA-specific IgA ELISA. Immunogenicity of the IsdA-CTA$_2$/B chimera was measured after intranasal delivery in dairy cows (FIGS. 14A-14E).

A. IsdA specific IgG serum titers of IsdA-CTA$_2$/B vaccinated cows (2472, 2340, 2319) and IsdA control vaccinated cows (2403, 2299, 2296).

Titers were calculated as the highest dilution 0.2 O.D. above background and were reported as a ratio with Day 0. Combined titers of IsdA-CTA$_2$/B vaccinated cows were significant over IsdA control vaccinated cows on day 49 (**Student's t-test, p–0.003)

B. IsdA specific IgG milk titers of IsdA-CTA2/B vaccinated cows (2472, 2340, 2319) and IsdA control vaccinated cows (2403, 2299, 2296).

Titers were calculated as the highest dilution 0.2 O.D. above background and are reported as a ratio with Day 0. Combined titers of IsdA-CTA$_2$/B vaccinated cows were significant over IsdA control vaccinated cows on days 14, 28, and 49 (*Student's t-test, p<0.05).

C. IsdA-specific IgA in milk from IsdA-CTA2/B vaccinated cows and IsdA vaccinated cows.

Levels were reported as the ratio of IsdA specific IgA over total IgA after the subtraction of Day 0 at a milk dilution of 1:8. No significant differences were detected between IsdA-CTA$_2$/B vaccinated cows and IsdA control vaccinated cows.

D. IsdA-specific IgA in nasal secretions from IsdA-CTA$_2$/B vaccinated cows and IsdA vaccinated cows.

Levels were reported as the ratio of IsdA specific IgA over total IgA after the subtraction of Day 0 at a nasal wash dilution of 1:8. No significant differences were detected between IsdA-CTA2/B vaccinated cows and IsdA control vaccinated cows.

E. Somatic cell counts throughout the study of IsdA-CTA$_2$/B vaccinated cows and IsdA vaccinated cows. No significant differences were detected between IsdA-CTA$_2$/B vaccinated cows and IsdA control vaccinated cows.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A chimeric protein capable of generating an immune response in a mammal comprising a truncated iron-regulated surface determinant B (IsdB) protein of *Staphylococcus aureus* consisting of amino acids 42-338 of SEQ ID NO: 23 and an adjuvant protein, wherein said adjuvant protein is cholera toxin subunit A2 (CTA2), cholera toxin subunit B (CTB), heat labile toxin subunit A2, heat labile toxin subunit B, Shiga toxin subunit A2, Shiga toxin subunit B, or any combination thereof.

2. The chimeric protein of claim 1, wherein said adjuvant protein is CTA2 and CTB.

3. The chimeric protein of claim 1, wherein said CTA2 has the amino acid sequence of SEQ ID NO: 2 or an amino acid sequence that is at least 90% identical thereto.

4. The chimeric protein of claim 1, wherein said CTB has the amino acid sequence of SEQ ID NO: 3 or an amino acid sequence that is at least 90% identical thereto.

5. The chimeric protein of claim 1, wherein the chimeric protein is a fusion protein.

6. The chimeric protein of claim 1, wherein the chimeric protein comprises amino acids 24-367 of SEQ ID NO: 22.

7. An immunogenic composition comprising the chimeric protein of claim 1.

8. The immunogenic composition of claim 7, wherein said adjuvant protein is CTA2 and CTB.

9. The immunogenic composition of claim 7, wherein said CTA2 has the amino acid sequence of SEQ ID NO: 2 or an amino acid sequence that is at least 90% identical thereto.

10. The immunogenic composition of claim 7, wherein said CTB has the amino acid sequence of SEQ ID NO: 3 or an amino acid sequence that is at least 90% identical thereto.

11. The immunogenic composition of claim 7, wherein the chimeric protein is a fusion protein.

12. The immunogenic composition of claim 7, wherein the chimeric protein comprises amino acids 24-367 of SEQ ID NO: 22.

13. A method of generating an immune response to *Staphylococcus aureus* in a mammal comprising administering to the mammal a composition comprising a chimeric protein, wherein the chimeric protein comprises a truncated iron-regulated surface determinant B (IsdB) protein of *Staphylococcus aureus* consisting of amino acids 42-338 of SEQ ID NO: 23 and an adjuvant protein, wherein said adjuvant protein is cholera toxin subunit A2 (CTA2), cholera toxin subunit B (CTB), heat labile toxin subunit A2, heat labile toxin subunit B, Shiga toxin subunit A2, Shiga toxin subunit B, or any combination thereof.

14. The method of claim 13, wherein said adjuvant protein is CTA2 and CTB.

15. The method of claim 13, wherein said CTA2 has the amino acid sequence of SEQ ID NO: 2 or an amino acid sequence that is at least 90% identical thereto.

16. The method of claim 13, wherein said CTB has the amino acid sequence of SEQ ID NO: 3 or an amino acid sequence that is at least 90% identical thereto.

17. The method of claim 13, wherein the chimeric protein is a fusion protein.

18. The method of claim 13, wherein the chimeric protein comprises amino acids 24-367 of SEQ ID NO: 22.

19. The method of claim 13, wherein the administration is by intranasal administration, oral administration, intramuscular administration, peritoneal administration, sublingual administration, transcutaneous administration, subcutaneous administration, intravaginal administration, intrarectal administration, intramammary administration, or any combination thereof.

20. The method of claim 13, wherein the mammal is a cow.

* * * * *

SEQUENCE LISTING

<160> NUMBER OF SEQ ID NOS: 26

<210> SEQ ID NO 1
<211> LENGTH: 193
<212> TYPE: PRT
<213> ORGANISM: Vibrio cholerae

<400> SEQUENCE: 1

Asn Asp Asp Lys Leu Tyr Arg Ala Asp Ser Arg Pro Pro Asp Glu Ile

```
1               5                   10                  15
Lys Gln Ser Gly Gly Leu Met Pro Arg Gly Gln Ser Glu Tyr Phe Asp
                20                  25                  30
Arg Gly Thr Gln Met Asn Ile Asn Leu Tyr Asp His Ala Arg Gly Thr
                35                  40                  45
Gln Thr Gly Phe Val Arg His Asp Asp Gly Tyr Val Ser Thr Ser Ile
        50                  55                  60
Ser Leu Arg Ser Ala His Leu Val Gly Gln Thr Ile Leu Ser Gly His
65                  70                  75                  80
Ser Thr Tyr Tyr Ile Tyr Val Ile Ala Thr Ala Pro Asn Met Phe Asn
                85                  90                  95
Val Asn Asp Val Leu Gly Ala Tyr Ser Pro His Pro Asp Glu Gln Glu
                100                 105                 110
Val Ser Ala Leu Gly Gly Ile Pro Tyr Ser Gln Ile Tyr Gly Trp Tyr
                115                 120                 125
Arg Val His Phe Gly Val Leu Asp Glu Gln Leu His Arg Asn Arg Gly
            130                 135                 140
Tyr Arg Asp Arg Tyr Tyr Ser Asn Leu Asp Ile Ala Pro Ala Ala Asp
145                 150                 155                 160
Gly Tyr Gly Leu Ala Gly Phe Pro Pro Glu His Arg Ala Trp Arg Glu
                165                 170                 175
Glu Pro Trp Ile His His Ala Pro Pro Gly Cys Gly Asn Ala Pro Arg
                180                 185                 190
Ser

<210> SEQ ID NO 2
<211> LENGTH: 47
<212> TYPE: PRT
<213> ORGANISM: Vibrio cholerae

<400> SEQUENCE: 2

Ser Met Ser Asn Thr Ser Asp Glu Lys Thr Gln Ser Leu Gly Val Lys
1               5                   10                  15
Phe Leu Asp Glu Tyr Gln Ser Lys Val Lys Arg Gln Ile Phe Ser Gly
                20                  25                  30
Tyr Gln Ser Asp Ile Asp Thr His Asn Arg Ile Lys Asp Glu Leu
            35                  40                  45

<210> SEQ ID NO 3
<211> LENGTH: 103
<212> TYPE: PRT
<213> ORGANISM: Vibrio cholerae

<400> SEQUENCE: 3

Thr Pro Gln Asn Ile Thr Asp Leu Cys Ala Glu Tyr His Asn Thr Gln
1               5                   10                  15
Ile His Thr Leu Asn Asp Lys Ile Phe Ser Tyr Thr Glu Ser Leu Ala
                20                  25                  30
Gly Lys Arg Glu Met Ala Ile Ile Thr Phe Lys Asn Gly Ala Thr Phe
            35                  40                  45
Gln Val Glu Val Pro Gly Ser Gln His Ile Asp Ser Gln Lys Lys Ala
        50                  55                  60
Ile Glu Arg Met Lys Asp Thr Leu Arg Ile Ala Tyr Leu Thr Glu Ala
65                  70                  75                  80
Lys Val Glu Lys Leu Cys Val Trp Asn Asn Lys Thr Pro His Ala Ile
                85                  90                  95
```

```
Ala Ala Ile Ser Met Ala Asn
            100
```

<210> SEQ ID NO 4
<211> LENGTH: 273
<212> TYPE: PRT
<213> ORGANISM: Staphylococcus aureus

<400> SEQUENCE: 4

```
Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Ala Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Ala Lys Pro Asn
    130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Ala
                165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
    210                 215                 220

Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys Gln Asn Glu
                245                 250                 255

Val His Lys Gln Gly Pro Ser Lys Asp Ser Lys Ala Lys Glu Leu Pro
            260                 265                 270

Lys
```

<210> SEQ ID NO 5
<211> LENGTH: 423
<212> TYPE: PRT
<213> ORGANISM: Artificial Sequence
<220> FEATURE:
<223> OTHER INFORMATION: Description of Artificial Sequence: Synthetic chimeric protein IsdA-CTA2/B polypeptide

<400> SEQUENCE: 5

```
Ala Thr Glu Ala Thr Asn

```
Gln Ala Thr Ser Gln Pro Ile Asn Phe Gln Val Gln Lys Asp Gly Ser
                20                  25                  30

Ser Glu Lys Ser His Met Asp Asp Tyr Met Gln His Pro Gly Lys Val
            35                  40                  45

Ile Lys Gln Asn Asn Lys Tyr Tyr Phe Gln Ala Val Leu Asn Asn Ala
        50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
                100                 105                 110

Ile Val Val Pro Gln Ile Asn Tyr Asn His Arg Tyr Thr Thr His Leu
            115                 120                 125

Glu Phe Glu Lys Ala Ile Pro Thr Leu Ala Asp Ala Ala Lys Pro Asn
        130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Ala
                165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
210                 215                 220

Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys Gln Asn Glu
                245                 250                 255

Val His Lys Gln Gly Pro Ser Lys Asp Ser Lys Ala Lys Glu Leu Pro
            260                 265                 270

Lys Ser Met Ser Asn Thr Ser Asp Glu Lys Thr Gln Ser Leu Gly Val
        275                 280                 285

Lys Phe Leu Asp Glu Tyr Gln Ser Lys Val Lys Arg Gln Ile Phe Ser
290                 295                 300

Gly Tyr Gln Ser Asp Ile Asp Thr His Asn Arg Ile Lys Asp Glu Leu
305                 310                 315                 320

Thr Pro Gln Asn Ile Thr Asp Leu Cys Ala Glu Tyr His Asn Thr Gln
                325                 330                 335

Ile His Thr Leu Asn Asp Lys Ile Phe Ser Tyr Thr Glu Ser Leu Ala
            340                 345                 350

Gly Lys Arg Glu Met Ala Ile Ile Thr Phe Lys Asn Gly Ala Thr Phe
        355                 360                 365

Gln Val Glu Val Pro Gly Ser Gln His Ile Asp Ser Gln Lys Lys Ala
370                 375                 380

Ile Glu Arg Met Lys Asp Thr Leu Arg Ile Ala Tyr Leu Thr Glu Ala
385                 390                 395                 400

Lys Val Glu Lys Leu Cys Val Trp Asn Asn Lys Thr Pro His Ala Ile
                405                 410                 415

Ala Ala Ile Ser Met Ala Asn
                420
```

<210> SEQ ID NO 6
<211> LENGTH: 320
<212> TYPE: PRT
<213> ORGANISM: Artificial Sequence
<220> FEATURE:
<223> OTHER INFORMATION: Description of Artificial Sequence: Synthetic chimeric protein Isda-CTA2 polypeptide

<400> SEQUENCE: 6

```
Ala Thr Gl

```
                1               5                    10                   15
            Lys Arg Ser Gly Gly Leu Met Pro Arg Gly His Asn Glu Tyr Phe Asp
                               20                   25                   30
            Arg Gly Thr Gln Met Asn Ile Asn Leu Tyr Asp His Ala Arg Gly Thr
                               35                   40                   45
            Gln Thr Gly Phe Val Arg Tyr Asp Asp Gly Tyr Val Ser Thr Ser Leu
                               50                   55                   60
            Ser Leu Arg Ser Ala His Leu Ala Gly Gln Ser Ile Leu Ser Gly Tyr
             65                 70                   75                   80
            Ser Thr Tyr Tyr Ile Tyr Val Ile Ala Thr Ala Pro Asn Met Phe Asn
                                85                  90                   95
            Val Asn Asp Val Leu Gly Val Tyr Ser Pro His Pro Tyr Glu Gln Glu
                               100                 105                  110
            Val Ser Ala Leu Gly Gly Ile Pro Tyr Ser Gln Ile Tyr Gly Trp Tyr
                               115                 120                  125
            Arg Val Asn Phe Gly Val Ile Asp Glu Arg Leu His Arg Asn Arg Glu
                               130                 135                  140
            Tyr Arg Asp Arg Tyr Tyr Arg Asn Leu Asn Ile Ala Pro Ala Glu Asp
             145                150                 155                  160
            Gly Tyr Arg Leu Ala Gly Phe Pro Pro Asp His Gln Ala Trp Arg Glu
                               165                 170                  175
            Glu Pro Trp Ile His His Ala Pro Gln Gly Cys Gly Asn Ser Ser Arg
                               180                 185                  190
            Thr

<210> SEQ ID NO 8
            <211> LENGTH: 47
            <212> TYPE: PRT
            <213> ORGANISM: Escherichia coli

<400> SEQUENCE: 8

Ile Thr Gly Asp Thr Cys Asn Glu Glu Thr Gln Asn Leu Ser Thr Ile
              1               5                   10                   15
            Tyr Leu Arg Lys Tyr Gln Ser Lys Val Lys Arg Gln Ile Phe Ser Asp
                               20                   25                   30
            Tyr Gln Ser Glu Val Asp Ile Tyr Asn Arg Ile Arg Asn Glu Leu
                            35                   40                   45

<210> SEQ ID NO 9
            <211> LENGTH: 103
            <212> TYPE: PRT
            <213> ORGANISM: Escherichia coli

<400> SEQUENCE: 9

Ala Pro Gln Ser Ile Thr Glu Leu Cys Ser Glu Tyr His Asn Thr Gln
              1               5                   10                   15
            Ile Tyr Thr Ile Asn Asp Lys Ile Leu Ser Tyr Thr Glu Ser Met Ala
                               20                   25                   30
            Gly Lys Arg Glu Met Val Ile Ile Thr Phe Lys Ser Gly Ala Thr Phe
                               35                   40                   45
            Gln Val Glu Val Pro Gly Ser Gln His Ile Asp Ser Gln Lys Lys Ala
                               50                   55                   60
            Ile Glu Arg Met Lys Asp Thr Leu Arg Ile Thr Tyr Leu Thr Glu Thr
             65                 70                   75                   80
            Lys Ile Asp Lys Leu Cys Val Trp Asn Asn Lys Thr Pro Asn Ser Ile
                               85                   90                   95
```

Ala Ala Ile Ser Met Glu Asn
            100

<210> SEQ ID NO 10
<211> LENGTH: 423
<212> TYPE: PRT
<213> ORGANISM: Artificial Sequence
<220> FEATURE:
<223> OTHER INFORMATION: Description of Artificial Sequence: Synthetic
      chimeric protein IsdA-LTA2/B polypeptide

<400> SEQUENCE: 10

Ala Thr Glu Ala Thr Asn Ala Thr Asn Gln Ser Thr Gln Val Ser
1               5                  10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
            35                  40                  45

Ile Lys Gln Asn Asn Lys Tyr Tyr Phe Gln Ala Val Leu Asn Asn Ala
        50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
            115                 120                 125

Glu Phe Glu Lys Ala Ile Pro Thr Leu Ala Asp Ala Ala Lys Pro Asn
    130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Lys Val Lys Pro Ala
                165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
    210                 215                 220

Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys Gln Asn Glu
                245                 250                 255

Val His Lys Gln Gly Pro Ser Lys Asp Ser Lys Ala Lys Glu Leu Pro
            260                 265                 270

Lys Ile Thr Gly Asp Thr Cys Asn Glu Glu Thr Gln Asn Leu Ser Thr
        275                 280                 285

Ile Tyr Leu Arg Lys Tyr Gln Ser Lys Val Lys Arg Gln Ile Phe Ser
    290                 295                 300

Asp Tyr Gln Ser Glu Val Asp Ile Tyr Asn Arg Ile Arg Asn Glu Leu
305                 310                 315                 320

Ala Pro Gln Ser Ile Thr Glu Leu Cys Ser Glu Tyr His Asn Thr Gln
                325                 330                 335

Ile Tyr Thr Ile Asn Asp Lys Ile Leu Ser Tyr Thr Glu Ser Met Ala

```
            340                 345                 350
Gly Lys Arg Glu Met Val Ile Ile Thr Phe Lys Ser Gly Ala Thr Phe
        355                 360                 365

Gln Val Glu Val Pro Gly Ser Gln His Ile Asp Ser Gln Lys Lys Ala
    370                 375                 380

Ile Glu Arg Met Lys Asp Thr Leu Arg Ile Thr Tyr Leu Thr Glu Thr
385                 390                 395                 400

Lys Ile Asp Lys Leu Cys Val Trp Asn Asn Lys Thr Pro Asn Ser Ile
                405                 410                 415

Ala Ala Ile Ser Met Glu Asn
            420
```

<210> SEQ ID NO 11
<211> LENGTH: 320
<212> TYPE: PRT
<213> ORGANISM: Artificial Sequence
<220> FEATURE:
<223> OTHER INFORMATION: Description of Artificial Sequence: Synthetic
      chimeric protein IsdA-LTA2 polypeptide

<400> SEQUENCE: 11

```
Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Ala Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Ala Lys Pro Asn
    130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Ala
                165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
    210                 215                 220

Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys Gln Asn Glu
                245                 250                 255

Val His Lys Gln Gly Pro Ser Lys Asp Ser Lys Ala Lys Glu Leu Pro
            260                 265                 270
```

```
Lys Ile Thr Gly Asp Thr Cys Asn Glu Glu Thr Gln Asn Leu Ser Thr
                275                 280                 285

Ile Tyr Leu Arg Lys Tyr Gln Ser Lys Val Lys Arg Gln Ile Phe Ser
            290                 295                 300

Asp Tyr Gln Ser Glu Val Asp Ile Tyr Asn Arg Ile Arg Asn Glu Leu
305                 310                 315                 320

<210> SEQ ID NO 12
<211> LENGTH: 250
<212> TYPE: PRT
<213> ORGANISM: Escherichia coli

<400> SEQUENCE: 12

Glu Phe Thr Leu Asp Phe Ser Thr Ala Lys Thr Tyr Val Asp Ser Leu
1               5                   10                  15

Asn Val Ile Arg Ser Ala Ile Gly Thr Pro Leu Gln Thr Ile Ser Ser
            20                  25                  30

Gly Gly Thr Ser Leu Leu Met Ile Asp Ser Gly Thr Gly Asp Asn Leu
        35                  40                  45

Phe Ala Val Asp Val Arg Gly Ile Asp Pro Glu Glu Gly Arg Phe Asn
    50                  55                  60

Asn Leu Arg Leu Ile Val Glu Arg Asn Asn Leu Tyr Val Thr Gly Phe
65                  70                  75                  80

Val Asn Arg Thr Asn Asn Val Phe Tyr Arg Phe Ala Asp Phe Ser His
                85                  90                  95

Val Thr Phe Pro Gly Thr Thr Ala Val Thr Leu Ser Gly Asp Ser Ser
            100                 105                 110

Tyr Thr Thr Leu Gln Arg Val Ala Gly Ile Ser Arg Thr Gly Met Gln
        115                 120                 125

Ile Asn Arg His Ser Leu Thr Thr Ser Tyr Leu Asp Leu Met Ser His
    130                 135                 140

Ser Gly Thr Ser Leu Thr Gln Ser Val Ala Arg Ala Met Leu Arg Phe
145                 150                 155                 160

Val Thr Val Thr Ala Glu Ala Leu Arg Phe Arg Gln Ile Gln Arg Gly
                165                 170                 175

Phe Arg Thr Thr Leu Asp Asp Leu Ser Gly Arg Ser Tyr Val Met Thr
            180                 185                 190

Ala Glu Asp Val Asp Leu Thr Leu Asn Trp Gly Arg Leu Ser Ser Val
        195                 200                 205

Leu Pro Asp Tyr His Gly Gln Asp Ser Val Arg Val Gly Arg Ile Ser
    210                 215                 220

Phe Gly Ser Ile Asn Ala Ile Leu Gly Ser Val Ala Leu Ile Leu Asn
225                 230                 235                 240

Cys His His His Ala Ser Arg Val Ala Arg
                245                 250

<210> SEQ ID NO 13
<211> LENGTH: 42
<212> TYPE: PRT
<213> ORGANISM: Escherichia coli

<400> SEQUENCE: 13

Met Ala Ser Asp Glu Phe Pro Ser Met Cys Pro Ala Asp Gly Arg Val
1               5                   10                  15

Arg Gly Ile Thr His Asn Lys Ile Leu Trp Asp Ser Thr Leu Gly
            20                  25                  30
```

```
Ala Ile Leu Met Arg Arg Thr Ile Ser Ser
            35                  40
```

<210> SEQ ID NO 14
<211> LENGTH: 69
<212> TYPE: PRT
<213> ORGANISM: Escherichia coli

<400> SEQUENCE: 14

```
Thr Pro Asp Cys Val Thr Gly Lys Val Glu Tyr Thr Lys Tyr Asn Asp
1               5                   10                  15

Asp Asp Thr Phe Thr Val Lys Val Gly Asp Lys Glu Leu Phe Thr Asn
            20                  25                  30

Arg Trp Asn Leu Gln Ser Leu Leu Leu Ser Ala Gln Ile Thr Gly Met
        35                  40                  45

Thr Val Thr Ile Lys Thr Asn Ala Cys His Asn Gly Gly Gly Phe Ser
    50                  55                  60

Glu Val Ile Phe Arg
65
```

<210> SEQ ID NO 15
<211> LENGTH: 384
<212> TYPE: PRT
<213> ORGANISM: Artificial Sequence
<220> FEATURE:
<223> OTHER INFORMATION: Description of Artificial Sequence: Synthetic
      chimeric protein IsdA-STA2/B polypeptide

<400> SEQUENCE: 15

```
Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Ala Val Leu Asn Asn Ala
    50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Ala Lys Pro Asn
    130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Glu Lys Val Lys Pro Ala
                165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205

Val Lys Thr Thr Gln Thr Ala Gln Asp Gln Asn Lys Val Gln Thr Pro
    210                 215                 220
```

```
Val Lys Asp Val Ala Thr Ala Lys Ser Glu Ser Asn Asn Gln Ala Val
225                 230                 235                 240

Ser Asp Asn Lys Ser Gln Gln Thr Asn Lys Val Thr Lys Gln Asn Glu
            245                 250                 255

Val His Lys Gln Gly Pro Ser Lys Asp Ser Lys Ala Lys Glu Leu Pro
        260                 265                 270

Lys Met Ala Ser Asp Glu Phe Pro Ser Met Cys Pro Ala Asp Gly Arg
    275                 280                 285

Val Arg Gly Ile Thr His Asn Lys Ile Leu Trp Asp Ser Ser Thr Leu
290                 295                 300

Gly Ala Ile Leu Met Arg Arg Thr Ile Ser Ser Thr Pro Asp Cys Val
305                 310                 315                 320

Thr Gly Lys Val Glu Tyr Thr Lys Tyr Asn Asp Asp Thr Phe Thr
                325                 330                 335

Val Lys Val Gly Asp Lys Glu Leu Phe Thr Asn Arg Trp Asn Leu Gln
                340                 345                 350

Ser Leu Leu Leu Ser Ala Gln Ile Thr Gly Met Thr Val Thr Ile Lys
            355                 360                 365

Thr Asn Ala Cys His Asn Gly Gly Phe Ser Glu Val Ile Phe Arg
370                 375                 380
```

<210> SEQ ID NO 16
<211> LENGTH: 315
<212> TYPE: PRT
<213> ORGANISM: Artificial Sequence
<220> FEATURE:
<223> OTHER INFORMATION: Description of Artificial Sequence: Synthetic
      chimeric protein IsdA-STA2 polypeptide

<400> SEQUENCE: 16

```
Ala Thr Glu Ala Thr Asn Ala Thr Asn Asn Gln Ser Thr Gln Val Ser
1               5                   10                  15

Gln Ala Thr Ser Gln Pro Ile Asn Phe Gln Val Gln Lys Asp Gly Ser
            20                  25                  30

Ser Glu Lys Ser His Met Asp Asp Tyr Met Gln His Pro Gly Lys Val
        35                  40                  45

Ile Lys Gln Asn Asn Lys Tyr Tyr Phe Gln Ala Val Leu Asn Asn Ala
50                  55                  60

Ser Phe Trp Lys Glu Tyr Lys Phe Tyr Asn Ala Asn Asn Gln Glu Leu
65                  70                  75                  80

Ala Thr Thr Val Val Asn Asp Asp Lys Lys Ala Asp Thr Arg Thr Ile
                85                  90                  95

Asn Val Ala Val Glu Pro Gly Tyr Lys Ser Leu Thr Thr Lys Val His
            100                 105                 110

Ile Val Val Pro Gln Ile Asn Tyr Asn His Arg Tyr Thr Thr His Leu
        115                 120                 125

Glu Phe Glu Lys Ala Ile Pro Thr Leu Ala Asp Ala Ala Lys Pro Asn
    130                 135                 140

Asn Val Lys Pro Val Gln Pro Lys Pro Ala Gln Pro Lys Thr Pro Thr
145                 150                 155                 160

Glu Gln Thr Lys Pro Val Gln Pro Lys Val Lys Val Lys Pro Ala
                165                 170                 175

Val Thr Ala Pro Ser Lys Asn Glu Asn Arg Gln Thr Thr Lys Val Val
            180                 185                 190

Ser Ser Glu Ala Thr Lys Asp Gln Ser Gln Thr Gln Ser Ala Arg Thr
        195                 200                 205
```

-continued

```
Val Lys Thr Thr Gln Thr Ala Gln Asp Gln Asn Lys Val Gln Thr Pro
    210                 215                 220
Val Lys Asp Val Ala Thr Ala Lys Ser Glu Ser Asn Asn Gln Ala Val
225                 230                 235                 240
Ser Asp Asn Lys Ser Gln Gln Thr Asn Lys Val Thr Lys Gln Asn Glu
                245                 250                 255
Val His Lys Gln Gly Pro Ser Lys Asp Ser Lys Ala Lys Glu Leu Pro
            260                 265                 270
Lys Met Ala Ser Asp Glu Phe Pro Ser Met Cys Pro Ala Asp Gly Arg
        275                 280                 285
Val Arg Gly Ile Thr His Asn Lys Ile Leu Trp Asp Ser Ser Thr Leu
    290                 295                 300
Gly Ala Ile Leu Met Arg Arg Thr Ile Ser Ser
305                 310                 315
```

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      5' SphI PCR primer

<400> SEQUENCE: 17
gctactggca tgcggcaaca gaagctacga ac         32

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      3' ClaI primer

<400> SEQUENCE: 18
gtgcatgatc gattttggta attctttagc            30

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      5' BamHI primer

<400> SEQUENCE: 19
gctactggat ccgcggcaac agaagctacg aac        33

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      5' BamHI alternative primer

<400> SEQUENCE: 20
gtgcataagc tttcaagttt ttggtaattc tttagc      36

<210> SEQ ID NO 21
<211> LENGTH: 30
<212> TYPE: DNA
<213> ORGANISM: Artificial Sequence

```
<220> FEATURE:
<223> OTHER INFORMATION: Description of Artificial Sequence: Synthetic
      3' HindIII primer

<400> SEQUENCE: 21
gtgcatgatc gattttggta attctttagc                                   30

<210> SEQ ID NO 22
<211> LENGTH: 367
<212> TYPE: PRT
<213> ORGANISM: Artificial Sequence
<220> FEATURE:
<223> OTHER INFORMATION: Description of Artificial Sequence: Synthetic
      chimeric protein IsdB-CTA2 polypeptide

<400> SEQUENCE: 22

Met Ser Phe Lys Lys Ile Ile Lys Ala Phe Val Ile Met Ala Ala Leu
1               5                   10                  15

Val Ser Val Gln Ala His Ala Ala Glu Glu Thr Gly Gly Thr Asn Thr
            20                  25                  30

Glu Ala Gln Pro Lys Thr Glu Ala Val Ala Ser Pro Thr Thr Thr Ser
        35                  40                  45

Glu Lys Ala Pro Glu Thr Lys Pro Val Ala Asn Ala Val Ser Val Ser
    50                  55                  60

Asn Lys Glu Val Glu Ala Pro Thr Ser Glu Thr Lys Glu Ala Lys Glu
65                  70                  75                  80

Val Lys Glu Val Lys Ala Pro Lys Glu Thr Lys Glu Val Lys Pro Ala
                85                  90                  95

Ala Lys Ala Thr Asn Asn Thr Tyr Pro Ile Leu Asn Gln Glu Leu Arg
            100                 105                 110

Glu Ala Ile Lys Asn Pro Ala Ile Lys Asp Lys Asp His Ser Ala Pro
        115                 120                 125

Asn Ser Arg Pro Ile Asp Phe Glu Met Lys Lys Lys Asp Gly Thr Gln
    130                 135                 140

Gln Phe Tyr His Tyr Ala Ser Ser Val Lys Pro Ala Arg Val Ile Phe
145                 150                 155                 160

Thr Asp Ser Lys Pro Glu Ile Glu Leu Gly Leu Gln Ser Gly Gln Phe
                165                 170                 175

Trp Arg Lys Phe Glu Val Tyr Glu Gly Asp Lys Lys Leu Pro Ile Lys
            180                 185                 190

Leu Val Ser Tyr Asp Thr Val Lys Asp Tyr Ala Tyr Ile Arg Phe Ser
        195                 200                 205

Val Ser Asn Gly Thr Lys Ala Val Lys Ile Val Ser Ser Thr His Phe
    210                 215                 220

Asn Asn Lys Glu Glu Lys Tyr Asp Tyr Thr Leu Met Glu Phe Ala Gln
225                 230                 235                 240

Pro Ile Tyr Asn Ser Ala Asp Lys Phe Lys Thr Glu Glu Asp Tyr Lys
                245                 250                 255

Ala Glu Lys Leu Leu Ala Pro Tyr Lys Lys Ala Lys Thr Leu Glu Arg
            260                 265                 270

Gln Val Tyr Glu Leu Asn Lys Ile Gln Asp Lys Leu Pro Glu Lys Leu
        275                 280                 285

Lys Ala Glu Tyr Lys Lys Lys Leu Glu Asp Thr Lys Lys Ala Leu Asp
    290                 295                 300

Glu Gln Val Lys Ser Ala Ile Thr Glu Phe Gln Asn Val Gln Pro Thr
305                 310                 315                 320
```

```
Ser Met Ser Asn Thr Ser Asp Glu Lys Thr Gln Ser Leu Gly Val Lys
            325                 330                 335

Phe Leu Asp Glu Tyr Gln Ser Lys Val Lys Arg Gln Ile Phe Ser Gly
            340                 345                 350

Tyr Gln Ser Asp Ile Asp Thr His Asn Arg Ile Lys Asp Glu Leu
            355                 360                 365

<210> SEQ ID NO 23
<211> LENGTH: 645
<212> TYPE: PRT
<213> ORGANISM: Staphylococcus aureus

<400> SEQUENCE: 23

Met Asn Lys Gln Gln Lys Glu Phe Lys Ser Phe Tyr Ser Ile Arg Lys
1               5                   10                  15

Ser Ser Leu Gly Val Ala Ser Val Ala Ile Ser Thr Leu Leu Leu Leu
            20                  25                  30

Met Ser Asn Gly Glu Ala Gln Ala Ala Glu Glu Thr Gly Gly Thr
            35                  40                  45

Asn Thr Glu Ala Gln Pro Lys Thr Glu Ala Val Ala Ser Pro Thr Thr
    50                  55                  60

Thr Ser Glu Lys Ala Pro Glu Thr Lys Pro Val Ala Asn Ala Val Ser
65                  70                  75                  80

Val Ser Asn Lys Glu Val Glu Ala Pro Thr Ser Glu Thr Lys Glu Ala
                85                  90                  95

Lys Glu Val Lys Glu Val Lys Ala Pro Lys Glu Thr Lys Glu Val Lys
            100                 105                 110

Pro Ala Ala Lys Ala Thr Asn Asn Thr Tyr Pro Ile Leu Asn Gln Glu
            115                 120                 125

Leu Arg Glu Ala Ile Lys Asn Pro Ala Ile Lys Asp Lys Asp His Ser
    130                 135                 140

Ala Pro Asn Ser Arg Pro Ile Asp Phe Glu Met Lys Lys Lys Asp Gly
145                 150                 155                 160

Thr Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
            180                 185                 190

Gln Phe Trp Arg Lys Phe Glu Val Tyr Glu Gly Asp Lys Lys Leu Pro
            195                 200                 205

Ile Lys Leu Val Ser Tyr Asp Thr Val Lys Asp Tyr Ala Tyr Ile Arg
    210                 215                 220

Phe Ser Val Ser Asn Gly Thr Lys Ala Val Lys Ile Val Ser Ser Thr
225                 230                 235                 240

His Phe Asn Asn Lys Glu Glu Lys Tyr Asp Tyr Thr Leu Met Glu Phe
                245                 250                 255

Ala Gln Pro Ile Tyr Asn Ser Ala Asp Lys Phe Lys Thr Glu Glu Asp
            260                 265                 270

Tyr Lys Ala Glu Lys Leu Leu Ala Pro Tyr Lys Lys Ala Lys Thr Leu
            275                 280                 285

Glu Arg Gln Val Tyr Glu Leu Asn Lys Ile Gln Asp Lys Leu Pro Glu
    290                 295                 300

Lys Leu Lys Ala Glu Tyr Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335
```

```
Pro Thr Asn Glu Lys Met Thr Asp Leu Gln Asp Thr Lys Tyr Val Val
            340                 345                 350

Tyr Glu Ser Val Glu Asn Asn Glu Ser Met Met Asp Thr Phe Val Lys
        355                 360                 365

His Pro Ile Lys Thr Gly Met Leu Asn Gly Lys Lys Tyr Met Val Met
    370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
            420                 425                 430

Val His Val Lys Thr Ile Asp Tyr Asp Gly Gln Tyr His Val Arg Ile
        435                 440                 445

Val Asp Lys Glu Ala Phe Thr Lys Ala Asn Thr Asp Lys Ser Asn Lys
    450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
        515                 520                 525

Pro Thr Lys Gly Glu Val Glu Ser Ser Ser Thr Thr Pro Thr Lys Val
    530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
        595                 600                 605

Ser Leu Pro Gln Thr Gly Glu Glu Ser Asn Lys Asp Met Thr Leu Pro
    610                 615                 620

Leu Met Ala Leu Leu Ala Leu Ser Ser Ile Val Ala Phe Val Leu Pro
625                 630                 635                 640

Arg Lys Arg Lys Asn
                645

<210> SEQ ID NO 24
<211> LENGTH: 347
<212> TYPE: PRT
<213> ORGANISM: Artificial Sequence
<220> FEATURE:
<223> OTHER INFORMATION: Description of Artificial Sequence: Synthetic
      chimeric protein ClfA-CTA2 polypeptide

<400> SEQUENCE: 24

Met Ser Phe Lys Lys Ile Ile Lys Ala Phe Val Ile Met Ala Ala Leu
1               5                   10                  15

Val Ser Val Gln Ala His Ala Gly Val Thr Ser Thr Ala Lys Val Pro
            20                  25                  30

Pro Ile Met Ala Gly Asp Gln Val Leu Ala Asn Gly Val Ile Asp Ser
```

```
                35                  40                  45
Asp Gly Asn Val Ile Tyr Thr Phe Thr Asp Tyr Val Asn Thr Lys Asp
 50                  55                  60

Asp Val Lys Ala Thr Leu Thr Met Pro Ala Tyr Ile Asp Pro Glu Asn
 65                  70                  75                  80

Val Lys Lys Thr Gly Asn Val Thr Leu Ala Thr Gly Ile Gly Ser Thr
                 85                  90                  95

Thr Ala Asn Lys Thr Val Leu Val Asp Tyr Glu Lys Tyr Gly Lys Phe
                100                 105                 110

Tyr Asn Leu Ser Ile Lys Gly Thr Ile Asp Gln Ile Asp Lys Thr Asn
            115                 120                 125

Asn Thr Tyr Arg Gln Thr Ile Tyr Val Asn Pro Ser Gly Asp Asn Val
130                 135                 140

Ile Ala Pro Val Leu Thr Gly Asn Leu Lys Pro Asn Thr Asp Ser Asn
145                 150                 155                 160

Ala Leu Ile Asp Gln Gln Asn Thr Ser Ile Lys Val Tyr Lys Val Asp
                165                 170                 175

Asn Ala Ala Asp Leu Ser Glu Ser Tyr Phe Val Asn Pro Glu Asn Phe
            180                 185                 190

Glu Asp Val Thr Asn Ser Val Asn Ile Thr Phe Pro Asn Pro Asn Gln
        195                 200                 205

Tyr Lys Val Glu Phe Asn Thr Pro Asp Gln Ile Thr Thr Pro Tyr
    210                 215                 220

Ile Val Val Val Asn Gly His Ile Asp Pro Asn Ser Lys Gly Asp Leu
225                 230                 235                 240

Ala Leu Arg Ser Thr Leu Tyr Gly Tyr Asn Ser Asn Ile Ile Trp Arg
                245                 250                 255

Ser Met Ser Trp Asp Asn Glu Val Ala Phe Asn Asn Gly Ser Gly Ser
            260                 265                 270

Gly Asp Gly Ile Asp Lys Pro Val Val Pro Glu Gln Pro Asp Glu Pro
        275                 280                 285

Gly Glu Ile Glu Pro Ile Pro Ser Arg Ser Thr Val Ser Met Ser Asn
    290                 295                 300

Thr Ser Asp Glu Lys Thr Gln Ser Leu Gly Val Lys Phe Leu Asp Glu
305                 310                 315                 320

Tyr Gln Ser Lys Val Lys Arg Gln Ile Phe Ser Gly Tyr Gln Ser Asp
                325                 330                 335

Ile Asp Thr His Asn Arg Ile Lys Asp Glu Leu
            340                 345

<210> SEQ ID NO 25
<211> LENGTH: 933
<212> TYPE: PRT
<213> ORGANISM: Staphylococcus aureus

<400> SEQUENCE: 25

Met Asn Met Lys Lys Lys Glu Lys His Ala Ile Arg Lys Lys Ser Ile
 1               5                  10                  15

Gly Val Ala Ser Val Leu Val Gly Thr Leu Ile Gly Phe Gly Leu Leu
                20                  25                  30

Ser Ser Lys Glu Ala Asp Ala Ser Glu Asn Ser Val Thr Gln Ser Asp
            35                  40                  45

Ser Ala Ser Asn Glu Ser Lys Ser Asn Asp Ser Ser Val Ser Ala
        50                  55                  60
```

-continued

```
Ala Pro Lys Thr Asp Asp Thr Asn Val Ser Asp Thr Lys Thr Ser Ser
 65                  70                  75                  80

Asn Thr Asn Asn Gly Glu Thr Ser Val Ala Gln Asn Pro Ala Gln Gln
                 85                  90                  95

Glu Thr Thr Gln Ser Ser Ser Thr Asn Ala Thr Thr Glu Glu Thr Pro
            100                 105                 110

Val Thr Gly Glu Ala Thr Thr Thr Thr Asn Gln Ala Asn Thr Pro
        115                 120                 125

Ala Thr Thr Gln Ser Ser Thr Asn Ala Glu Glu Leu Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
                165                 170                 175

Asp Thr Ser Thr Glu Ala Thr Pro Ser Asn Asn Glu Ser Ala Pro Gln
            180                 185                 190

Ser Thr Asp Ala Ser Asn Lys Asp Val Val Asn Gln Ala Val Asn Thr
        195                 200                 205

Ser Ala Pro Arg Met Arg Ala Phe Ser Leu Ala Ala Val Ala Ala Asp
    210                 215                 220

Ala Pro Ala Ala Gly Thr Asp Ile Thr Asn Gln Leu Thr Asn Val Thr
225                 230                 235                 240

Val Gly Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
            260                 265                 270

Asp Thr Phe Lys Ile Thr Val Pro Lys Glu Leu Asn Leu Asn Gly Val
        275                 280                 285

Thr Ser Thr Ala Lys Val Pro Pro Ile Met Ala Gly Asp Gln Val Leu
    290                 295                 300

Ala Asn Gly Val Ile Asp Ser Asp Gly Asn Val Ile Tyr Thr Phe Thr
305                 310                 315                 320

Asp Tyr Val Asn Thr Lys Asp Asp Val Lys Ala Thr Leu Thr Met Pro
                325                 330                 335

Ala Tyr Ile Asp Pro Glu Asn Val Lys Lys Thr Gly Asn Val Thr Leu
            340                 345                 350

Ala Thr Gly Ile Gly Ser Thr Thr Ala Asn Lys Thr Val Leu Val Asp
        355                 360                 365

Tyr Glu Lys Tyr Gly Lys Phe Tyr Asn Leu Ser Ile Lys Gly Thr Ile
    370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Ile Ala Pro Val Leu Thr Gly Asn Leu
                405                 410                 415

Lys Pro Asn Thr Asp Ser Asn Ala Leu Ile Asp Gln Gln Asn Thr Ser
            420                 425                 430

Ile Lys Val Tyr Lys Val Asp Asn Ala Ala Asp Leu Ser Glu Ser Tyr
        435                 440                 445

Phe Val Asn Pro Glu Asn Phe Glu Asp Val Thr Asn Ser Val Asn Ile
    450                 455                 460

Thr Phe Pro Asn Pro Asn Gln Tyr Lys Val Glu Phe Asn Thr Pro Asp
465                 470                 475                 480

Asp Gln Ile Thr Thr Pro Tyr Ile Val Val Val Asn Gly His Ile Asp
```

```
            485                 490                 495
Pro Asn Ser Lys Gly Asp Leu Ala Leu Arg Ser Thr Leu Tyr Gly Tyr
            500                 505                 510

Asn Ser Asn Ile Ile Trp Arg Ser Met Ser Trp Asp Asn Glu Val Ala
            515                 520                 525

Phe Asn Asn Gly Ser Gly Ser Gly Asp Gly Ile Asp Lys Pro Val Val
            530                 535                 540

Pro Glu Gln Pro Asp Glu Pro Gly Glu Ile Glu Pro Ile Pro Glu Asp
545                 550                 555                 560

Ser Asp Ser Asp Pro Gly Ser Asp Ser Gly Ser Asp Ser Asn Ser Asp
                565                 570                 575

Ser Gly Ser Asp Ser Gly Ser Asp Ser Thr Ser Asp Ser Gly Ser Asp
                580                 585                 590

Ser Ala Ser Asp Ser Asp Ser Ala Ser Asp Ser Asp Ser Ala Ser Asp
                595                 600                 605

Ser Asp Ser Ala Ser Asp Ser Ala Ser Asp Ser Asp Ser Asp
                610                 615                 620

Asn Asp Ser Asp Ser Asp Ser Asp Ser Asp Ser Asp Ser Asp Ser Asp
625                 630                 635                 640

Ser Asp Ser Asp Ser Asp Ser Asp Ser Asp Ser Asp Ser Asp Ser Asp
                645                 650                 655

Ser Asp Ser Asp Ser Asp Ser Asp Ser Asp Ser Asp Ser Asp Ser Asp
                660                 665                 670

Ser Asp Ser Asp Ser Asp Ser Asp Ser Asp Ser Asp Ser Asp Ser Asp
                675                 680                 685

Ser Asp Ser Asp Ser Asp Ser Asp Ser Asp Ser Asp Ser Asp Ser Asp
                690                 695                 700

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
                725                 730                 735

Ser Asp Ser Asp Ser Asp Ser Asp Ser Asp Ser Asp Ser Asp Ser Asp
                740                 745                 750

Ser Asp Ser Asp Ser Asp Ser Asp Ser Asp Ser Asp Ser Asp Ser Ala
                755                 760                 765

Ser Asp Ser Asp Ser Asp Ser Asp Ser Asp Ser Asp Ser Asp Ser Asp
                770                 775                 780

Ser Asp Ser Asp Ser Asp Ser Asp Ser Asp Ser Asp Ser Asp Ser Asp
785                 790                 795                 800

Ser Asp Ser Asp Ser Asp Ser Glu Ser Asp Ser Asp Ser Glu Ser Asp
                805                 810                 815

Ser Asp Ser Asp Ser Asp Ser Asp Ser Asp Ser Asp Ser Asp Ser Asp
                820                 825                 830

Ser Asp Ser Asp Ser Ala Ser Asp Ser Asp Ser Gly Ser Asp Ser Asp
                835                 840                 845

Ser Ser Ser Asp Ser Asp Ser Glu Ser Asp Ser Asn Ser Asp Ser Glu
                850                 855                 860

Ser Gly Ser Asn Asn Asn Val Val Pro Pro Asn Ser Pro Lys Asn Gly
865                 870                 875                 880

Thr Asn Ala Ser Asn Lys Asn Glu Ala Lys Asp Ser Lys Glu Pro Leu
                885                 890                 895

Pro Asp Thr Gly Ser Glu Asp Glu Ala Asn Thr Ser Leu Ile Trp Gly
                900                 905                 910
```

```
Leu Leu Ala Ser Ile Gly Ser Leu Leu Leu Phe Arg Arg Lys Lys Glu
        915                 920                 925

Asn Lys Asp Lys Lys
    930

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 26

His His His His His His
1               5
```